United States Patent
Ciabarra, Jr. et al.

(10) Patent No.: US 12,400,037 B2
(45) Date of Patent: Aug. 26, 2025

(54) SYSTEMATIC IDENTIFICATION AND MASKING OF PRIVATE DATA FOR REPLAYING USER SESSIONS

(71) Applicant: Quantum Metric, Inc., Colorado Springs, CO (US)

(72) Inventors: Mario Luciano Ciabarra, Jr., Colorado Springs, CO (US); Adam Dille, Monument, CO (US); Sean De La Torre, Dana Point, CA (US)

(73) Assignee: Quantum Metric, Inc., Colorado Springs, CO (US)

( * ) Notice: Subject to any disclaimer, the term of this patent is extended or adjusted under 35 U.S.C. 154(b) by 229 days.

(21) Appl. No.: 17/943,782

(22) Filed: Sep. 13, 2022

(65) Prior Publication Data

US 2023/0090108 A1 Mar. 23, 2023

Related U.S. Application Data

(60) Provisional application No. 63/247,569, filed on Sep. 23, 2021.

(51) Int. Cl.
*G06F 21/62* (2013.01)
*H04L 67/50* (2022.01)

(52) U.S. Cl.
CPC ...... *G06F 21/6263* (2013.01); *G06F 21/6254* (2013.01); *H04L 67/535* (2022.05)

(58) Field of Classification Search
None
See application file for complete search history.

(56) References Cited

U.S. PATENT DOCUMENTS

| | | | |
|---|---|---|---|
| 11,184,406 B1 * | 11/2021 | Shashank | H04L 67/1095 |
| 11,979,383 B1 * | 5/2024 | Litty | H04L 63/0281 |
| 2013/0132833 A1 * | 5/2013 | White | G06F 3/048 |
| | | | 715/704 |
| 2013/0276136 A1 * | 10/2013 | Goodwin | G06F 21/62 |
| | | | 726/27 |
| 2014/0115712 A1 * | 4/2014 | Powell | G06F 21/6263 |
| | | | 726/26 |
| 2014/0282464 A1 * | 9/2014 | El-Gillani | G06F 16/00 |
| | | | 713/189 |

(Continued)

OTHER PUBLICATIONS

International Application No. EP22196225.1, "Extended European Search Report", mailed Feb. 8, 2023, 7 pages.

*Primary Examiner* — Jerry B Dennison
(74) *Attorney, Agent, or Firm* — Kilpatrick Townsend & Stockton LLP

(57) ABSTRACT

Techniques are described herein for identifying and masking instances of private information in tracked user interactions with a network site during a network session. A scanning module can receive set of captured user interactions (e.g., movements between portions of the network site and data provided in one or more fields on the network site) with the network site during the network session. Instances of private information can be identified and a number of nodes in a document object model (DOM) for the network site that correspond to each identified instance of private information. Information about each corresponding node can be provided to update a capture agent to mask each corresponding node in future user interactions.

20 Claims, 8 Drawing Sheets

(56) References Cited

U.S. PATENT DOCUMENTS

| | | | |
|---|---|---|---|
| 2015/0339479 A1* | 11/2015 | Wang | G06F 40/174 726/22 |
| 2016/0127289 A1* | 5/2016 | Papa | G06Q 30/0255 709/206 |
| 2016/0188548 A1* | 6/2016 | Ciabarra, Jr. | G06F 40/123 715/234 |
| 2016/0203337 A1* | 7/2016 | Dubovský | G06F 21/6263 726/30 |
| 2017/0185368 A1 | 6/2017 | Handrigan et al. | |
| 2017/0323026 A1 | 11/2017 | Le Bras et al. | |
| 2018/0173375 A1* | 6/2018 | Webber | G06F 3/0481 |
| 2019/0146616 A1 | 5/2019 | White et al. | |
| 2019/0172499 A1* | 6/2019 | Bodziony | G06F 16/74 |
| 2020/0151348 A1* | 5/2020 | Chauhan | H04L 67/53 |
| 2020/0349289 A1* | 11/2020 | Roundtree | G06F 16/9566 |
| 2021/0067492 A1* | 3/2021 | Mastracci | H04L 63/0254 |
| 2021/0243233 A1* | 8/2021 | Singh | H04L 63/0435 |
| 2022/0350919 A1* | 11/2022 | Chouman | G06F 21/6245 |
| 2022/0360607 A1* | 11/2022 | Amiga | H04L 63/20 |
| 2023/0090108 A1* | 3/2023 | Ciabarra, Jr. | G06F 21/6254 726/26 |
| 2023/0216835 A1* | 7/2023 | Hoffman | H04L 51/04 726/26 |

* cited by examiner

SYSTEMATIC IDENTIFICATION AND MASKING OF PRIVATE DATA FOR REPLAYING USER SESSIONS

CROSS-REFERENCE TO RELATED APPLICATION

The present application is a non-provisional of, and claims the benefit and priority under 35 U.S.C. 119(e) of U.S. Provisional Application No. 63/247,569, filed Sep. 23, 2021, the entire disclosure of which is incorporated by reference herein in its entirety.

BACKGROUND

The present disclosure relates generally to processing user interactions with a website during a web session and masking private information provided during the web session. Typically, a user can interact with a website that includes one or more web pages by interacting with one or more interfaces navigating the user across the web pages. During the web session, the user can provide one or more instances of private information, such as logging into an account or providing an e-mail address or phone number when requesting information from the entity associated with the website.

In many instances, when a user (e.g., a website visitor) is browsing the website, certain issues can arise, such as a delay in loading a webpage of the website or a broken webpage of the website. This may frustrate the user and cause the user to abandon the website or stop performing specific actions on the website. Because of these issues, the user may be less likely to stay on the website and perform specific actions on the website.

In order to identify such issues, user interactions with the website during a web session can be monitored and/or stored for subsequent processing. As digital monitoring of user interactions on websites becomes more common, private information provided by the user may also be captured. The user interactions that include the captured private information may be transmitted to other computing devices for processing and/or storage, which may leave the private information vulnerable to unauthorized access. Therefore, there is a need for improved systems and methods to detect and mask (e.g., encrypt, remove) private information in user interactions with the website.

SUMMARY

Techniques are described herein for masking private information captured during user interactions with a network site during a web session. The private information can be identified dynamically (e.g., using session data) so that a masking module can be updated to mask such data in future sessions. Besides tracking user interactions during a web session, private information in the tracked user interactions can be identified (e.g., using tags provided in a blacklist) and masked to prevent unauthorized access to the private information in subsequent processing of the tracked user interactions, thereby leading to a solution. For example, each identified instance of private information identified in the tracked user interactions can correspond to a node in a document object model (DOM). A capture agent can mask the private information in the corresponding nodes, e.g., those listed in a black list in subsequent user interactions with the network site.

A problem with masking such private information is that the web documents can change, thereby changing which node private information is in. Embodiments can address such a problem by dynamically identifying private information in session data at a server (e.g., a detection system), and then use a browser module to identify the corresponding node. Data relating to (e.g., identifying) the corresponding node(s) can then be pushed to a user device for masking via a capture agent, which may be sent by the server.

In an illustrative embodiment, a scanning module can analyze a set of captured user interactions with the network site, e.g., that were captured during the web session using a capture agent on a user device. As examples, the set of captured user interactions can include movements between portions of the network site and data provided in one or more fields on the network site. The scanning module can identify instances of private information being included in the set of captured user interactions with the network site. An example instance of private information can include data (e.g., username, address, email address, phone number) provided by a user in various fields in the network site during a web session. A timestamp can be assigned to each identified instance of private information that can indicate a time of each instance of private information provided during the set of captured user interactions with the network site.

The session data (e.g., changes to a DOM) for the network site can be loaded into a browser module. The DOM can include an object-oriented structure of nodes providing style, content, and format for each webpage comprising the web site. The changes to the DOM can correspond to the set of captured user interactions. A corresponding node in the DOM can be identified for each of the instances of private information using the timestamp assigned to each of the instances of private information. Information about each corresponding node can be provided as part of updating the capture agent to mask the corresponding node in future user interactions sent to the server Other embodiments are directed to systems and computer readable media associated with methods described herein. A better understanding of the nature and advantages of embodiments of the present invention may be gained with reference to the following detailed description and the accompanying drawings.

TERMS

Figure 1:
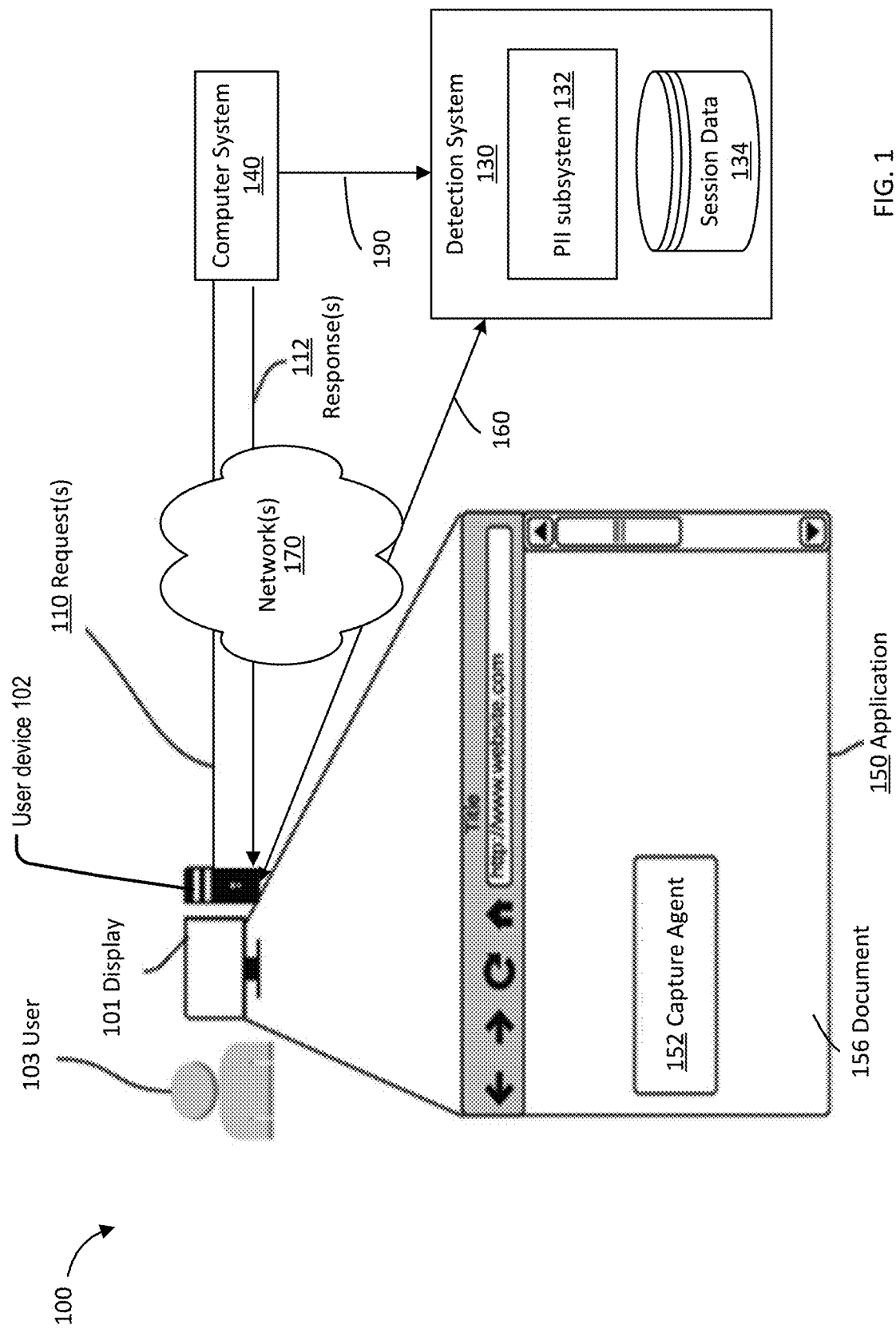
FIG. 1 illustrates an example of a distributed system for masking private information in tracked user interactions with a website, according to certain embodiments described herein.

Prior to further describing embodiments of the disclosure, description of related terms is provided.

A "user" may include an individual that uses a website using a user device. The user may also be referred to as a "consumer" or "customer" depending on the type of the website.

A "client" may include an individual or entity that owns a website. The client may also be responsible for maintaining and presenting the website to a user. The client may employ some individuals (e.g., web developers) for the purpose of maintaining the website. The client may also be referred to as a "website owner" or "website provider." A website can refer to a publicly available server on the world wide web or any network site that is accessible on a network (e.g., by a native application), such as the Internet. A website and a network site can be used interchangeably for the purpose of this application.

A "user device" may comprise any suitable computing device that can be used for communication. A user device may also be referred to as a "communication device." A user device may provide remote or direct communication capabilities. Examples of remote communication capabilities include using a mobile phone (wireless) network, wireless data network (e.g., 3G, 4G or similar networks), Wi-Fi, Wi-Max, or any other communication medium that may provide access to a network such as the Internet or a private network. Examples of user devices include desktop computers, mobile phones (e.g., cellular phones), PDAs, tablet computers, net books, laptop computers, etc. Further examples of user devices include wearable devices, such as smart watches, fitness bands, ankle bracelets, etc., as well as automobiles with remote or direct communication capabilities. A user device may comprise any suitable hardware and software for performing such functions and may also include multiple devices or components (e.g., when a device has remote access to a network by tethering to another device—i.e., using the other device as a modem—both devices taken together may be considered a single communication device).

A "client device" may comprise any suitable computing device that can be used for communication. The client device may be a computing device of an administrator of a web server hosting a website. A client device can include similar types of devices as a user device.

A "server computer" may include a powerful computer or cluster of computers. For example, the server computer can be a large mainframe, a minicomputer cluster, or a group of computers functioning as a unit. In some cases, the server computer may function as a web server or a database server. The server computer may include any hardware, software, other logic, or combination of the preceding for servicing the requests from one or more other computers. The term "computer system" may generally refer to a system including one or more server computers.

A "processor" or "processor circuit" may refer to any suitable data computation device or devices. A processor may comprise one or more microprocessors working together to accomplish a desired function. The processor may include a CPU that comprises at least one high-speed data processor adequate to execute program components for executing user and/or system-generated requests. The CPU may be a microprocessor such as AMD's Athlon, Duron and/or Opteron, etc.; IBM and/or Motorola's PowerPC; IBM's and Sony's Cell processor; Intel's Celeron, Itanium, Pentium, Xeon, and/or Xscale, etc.; and/or the like processor(s).

A "memory" or "system memory" may be any suitable device or devices that can store electronic data. A suitable memory may comprise a non-transitory computer readable medium that stores instructions that can be executed by a processor to implement a desired method. Examples of memories may comprise one or more memory chips, disk drives, etc. Such memories may operate using any suitable electrical, optical, and/or magnetic mode of operation.

A "session" or a "web session" or a "network sessions" general refers to a set of user interactions with a website, which can include any user-accessible server, e.g., that may be accessed by a web browser or native application. The session may include interactions starting with a user accessing a webpage of the website (e.g., using a web browser or other software application, e.g., a native application) and ending with the user ceasing interactions with the website (e.g., closing a webpage of the website within the web browser or software application). The time-length of the session in seconds, minutes, and/or hours can be determined based on a start time when the user first interacted with the website to an end time of the last interaction made by the user. The web server hosting the website may store an identifier of the session and other information associated with the session (e.g., elements or items of the website selected by the user, or information input by the user).

A "session event" or "web session event" may be measured for a session of a user device with a website. Examples of session events include errors, clicks, or user-defined events. An anomalous event may refer to an event type that occurs too much or too little during a time-window relative to an expected amount (e.g., a historical amount) for the time-window.

A "network operation" generally refers to an operation performed by a client device (e.g., a web server) to load or display a webpage on a user device. The network operation may be an event that occurred during a web session. In an example implementation, a timing metric may include timing values involving network operations that occurred during a web session. For example, for a page load time metric, timing values involving certain network operations such as a requesting a webpage, processing of a webpage using a Transmission Control Protocol (TCP) protocol, and looking up a webpage on a Domain Name Server (DNS) may be combined. If looking up the webpage on the DNS takes too long then the rest of the processes involved in loading the webpage may be delayed as well. Accordingly, a specific network operation may be responsible for a slow connection experience for a user which led the user to abandon a website or terminate a web session.

The term "providing" may include sending, transmitting, displaying or rendering, making available, or any other suitable method. While not necessarily described, messages communicated between any of the computers, networks, and devices described herein may be transmitted using a secure communications protocols such as, but not limited to, File Transfer Protocol (FTP); HyperText Transfer Protocol (HTTP); Secure Hypertext Transfer Protocol (HTTPS), Secure Socket Layer (SSL), ISO (e.g., ISO 8583) and/or the like.

DETAILED DESCRIPTION

Users of websites and software applications can experience issues such as a delay in loading a webpage, software bugs, or interface design flaws that hinder them from taking certain actions (e.g., registering for a website or placing an order). In some cases, the issue may cause the user to abandon the website out of frustration or the user may not be able to access the website. Such issues may not be identified by a web server hosting the website because the issues arise out of the generating and rendering of a webpage by the user's browser on a user device over Application Programming Interface (API) calls by the user's browser.

Techniques for identifying issues arising in interacting with a website may include monitoring user activities across the entire website. One could generally track user activities on the website (e.g., using a capture agent) and store the user activities during the web session. In many instances, the tracked user activities can be transmitted from a first computing device (e.g., a user computer) to another computing device (e.g., a remote server) for processing the tracked user activities. The tracked user activities on the website can be replayed or subsequently processed to derive insights into the user activities, such as identifying an interface design flaw that caused the user to abandon the website, for example.

Tracking user activities on a website during a web session can include tracking/storing private information. For instance, as a user logs into a portal associated with the website, the user can provide a username and a password. As another example, the user can provide identifying details (e.g., an e-mail address, phone number, name) to receive a newsletter from the website (e.g., via the provided e-mail address) or request other information from an entity associated with the website.

However, transmitting the tracked user activities that include instances of private information to other computing devices can leave the private information vulnerable to unauthorized access. For instance, as tracked user activities with the private information are transmitted to a remote computing device for processing, an unauthorized entity can access the private information. Thus, it is desirable to identify and mask private information in tracked user activities to maintain security of the private information.

Further, if a website was static, particular fields containing private information can be identified (e.g., using a Cascading Style Sheets (CSS) tag) and a computing device can be programmed to mask data corresponding with such tags. However, as aspects of websites change, the tags used to identify the private information can become out of date. It can be a labor-intensive process to interact with a website and repeatedly update the tags for the website to reflect new changes to the website. Thus, it is desirable to provide improvements for updating a capture agent to better mask private information, given the continuous changes that websites undergo.

The embodiments disclosed herein provide improved systems and methods to mask private information (e.g., or Personally Identifiable Information (PII)) included in captured user interactions with a website. Some embodiments can learn new instances of private information being used for a website and updating a capture agent to identify the new instances of private information. Various types of masking can be performed. For example, a first masking action can include encrypting a first number of private information types (e.g., email address, phone number) to allow for future access to such information, while a second masking action can include removing a second number of private information types (e.g., billing information) to prevent any subsequent access to such information Some embodiments can receive user interactions with a website and identify nodes in a document object model (DOM) structure for the website that correspond to time-stamped portions of the website containing private information. The identified node(s) (e.g., including a CSS tag) can also be provided in a notification to an administrator, e.g., to confirm the data really is private information. The administrator can then update a capture agent such that the identified node can be masked (e.g., encrypted or removed based on a type of private information). If certain criteria is satisfied (e.g., the same node is identified to have PII in at least a threshold number of previous network sessions), information about the node can be added to a blacklist in the capture agent, so that the data is masked.

Some embodiments can detect false positive instances of identified private information and prevent the masking of such fields. For example, a customer service phone number on a website can be identified as potentially comprising private information but comprises a false positive instance of identified private information. Masking of such fields can be prevented to increase efficiency in identifying and masking fields that include private information.

I. Capturing User Activity on a Website

FIG. 1 illustrates a generalized example of a system 100 as a high-level architectural diagram for a detection system. One or more of the below-described techniques may be implemented in or involve one or more computer systems. System 100 is not intended to suggest any limitation as to scope of use or functionality of described embodiments.

The system 100 may include one or more user devices, clients, or client systems (e.g., client application or client device), such as a user device 102. System 100 may include a computer system 140 (e.g., a web server computer). Clients may be operated by users, such as user 103. Computer system 140 may be operated by a user (e.g., an administrator). Clients can communicate with computer system 140 to exchange data via one or more communication networks (e.g., a network 170). Examples of a communication network include, without restriction, the Internet, a wide area network (WAN), a local arear network (LAN), an Ethernet network, a public or private network, a wired network, a wireless network, and the like, and combinations thereof.

Communications between clients and computer system 140 may include one or more requests 110 and/or one or more responses 112. A communication session (e.g., a web session) may be established between user device 102 and computer system 140 to exchange communications via network 170. Computer system 140 may be implemented to store electronic documents, such as a collection of web documents for a website. In some embodiments, clients may communicate with computer system 140 by transmitting a request 110 along network 170 to computer system 140. For example, a request from user device 102 to computer system 140 may be a request for an electronic document (e.g., a webpage) accessed from a URL at user device 102. A response 105 from a computer system 140 to user device 102 may be a response providing the webpage requested by user device 102. The communications exchanged in system 100 may be transmitted via one or more data packets. Data packet(s) that are received may be reassembled to yield a communication, such as a request or a response. Requests and responses may be transmitted via one or more network devices.

Requests and responses may include data, such as consumer data and/or enterprise data. The data may include an electronic document (also referred to herein as "a document"). Data as disclosed herein may be referred to as "cloud data," which is distinguishable as data in a cloud-based environment. An electronic document (also referred to herein as a "document" accessed on the Internet (e.g., the web) may be referred to herein as a document of a website. For example, an electronic document may be a "web document" or a "webpage" of a website. Data may be received from a computer system, data may be sent to a computer system, data may be processed by a computer system, or combinations thereof. Cloud data and/or enterprise data may be distinguishable from consumer data for consumer applications and/or services. Cloud data may include data accessed in a system including an enterprise system.

In certain embodiments, data may include data processed, stored, used, or communicated by an application or a service executing in a computer system. For example, data includes objects. Data may be in a format, such as a JSON (JavaScript Object Notation) format from enterprise applications. Data may include structured data (e.g., key value pairs), unstructured data (e.g., internal data processed or used by an application, data in JSON format, social posts, conversation streams, activity feeds, etc.), binary large objects (BLOBs), documents, system folders (e.g., application related folders in a sandbox environment), data using representational state transfer (REST) techniques (referred to herein as "RESTful data"), system data, configuration data, synchronization data, or combinations thereof.

In some embodiments, data in communications 110, 112 may include a resource such as a document as referenced herein. A resource, such as a document, may include a document extended markup language (XML) files, HTML files (e.g., a webpage), JavaScript files, visual assets, configuration files, media assets, a content item, etc., or a combination thereof. For example, a resource may be a webpage in an HTML format referenced by uniform resource information (URI), e.g., a uniform resource locator (URL). A BLOB may include a collection of binary data stored as a single entity in a database management system, such as an image, multimedia object, or executable code, or as otherwise known in the art.

System 100 can include a detection system 130 that performs techniques disclosed herein for detecting webpage data (e.g., events) associated with web sessions involving a website. In some embodiments, a detection system may be implemented at user device 102, detection system 130, or a combination thereof. Detection system 130 may provide a service or an application that enables a user to detect events. Detection system 130 may be implemented as part of user device 102, computer system 140, or a combination thereof. Detection system 130 may be communicatively coupled (e.g., via a network 170) to one or more elements in system 100. For example, detection system 130 may be communicatively coupled to user device 102 via connection 160 through network 170. Detection system 130 can be communicatively coupled to computer system 140 via network 170, e.g., depicted as connection 190. Such connections (e.g., 160 and 190) may occur through a common network device or via different network devices.

The detection system 130 may further include PII subsystem 132 and session data 134. PII subsystem 132 can be executed on a computing device (e.g., a server) and can identify instances of private information in tracked user interactions with a website during a web session as described herein. For example, the PII subsystem 132 can process session data 134 and identify the instances of private information in the set of user interactions, and identify nodes in a DOM for the website that correspond to the instances of private information. The session data 134 can include a number of tracked user interactions with a website, each set of tracked user interactions including a series of session events and/or network operations specifying interactions by the user with the website. The PII subsystem 132 can send instructions that include the corresponding nodes to the capture agent(s) 152 to mask the private information as described herein.

Detection system 130, computer system 140, and user device 102 may comprise one or more computers and/or servers which may be general purpose computers, specialized server computers (including, by way of example, PC servers, UNIX servers, mid-range servers, mainframe computers, rack-mounted servers, etc.), server farms, server clusters, distributed servers, or any other appropriate arrangement and/or combination thereof. Detection system 130 may run any of operating systems or a variety of additional server applications and/or mid-tier applications, including HTTP servers, FTP servers, CGI servers, Java servers, database servers, and the like. Exemplary database servers include without limitation those commercially available from Microsoft, and the like. Detection system 130 may be implemented using hardware, firmware, software, or combinations thereof. In one example, detection system 130 may include or implement a service (e.g., a Software as a Service, an Infrastructure as a Service, or a Platform as a Service) or a product (e.g., a computer program product) provided by Quantum Metric, LLC. In various embodiments, detection system 130 may be configured to run one or more services or software applications described in the foregoing disclosure. For example, detection system 130 may perform processing as disclosed herein according to an embodiment of the present disclosure.

User device 102 may include or be coupled to a display 101. User device 102 may provide access to one or more applications, such as application 150. Application 150 may be a browser enabling user 103 to view resources, such as documents. In at least one embodiment, system 100 may include a capture agent 152 that can detect events in system 100. Capture agent 152 may operate in communication with detection system 130 to provide a service or an application that enables a user to detect events.

Capture agent 152 may be implemented with program code (e.g., an application) that resides on user device 102, detection system 130, computer system 140, or a combination thereof. For example, capture agent 152 may be implemented using JavaScript that is embedded in a document 156 (e.g., a webpage) of a website that can identify and obtain data that is displayed at user device 102. Capture agent 152 may be client-side such that it is implemented at user device 102. Capture agent 152 can be sent in communications to user device 102. For example, the capture agent 152 can be retrieved from a third party server (e.g., from detection system 130) according to a link provided in the website provided from computer system 140. Capture agent 152 may communicate with detection system 130 to coordinate event detection. Capture agent 152 may perform operations disclosed herein as being performed by a client. In some embodiments, capture agent 152 may be received from detection system 130. Capture agent 152 may be deployed to user device 102 as part of a service provided by detection system 130. Capture agent 152 may be configured for communication with detection system 130. Capture agent 152 may gather data on behalf of detection system 130. In some embodiments, capture agent 152 may perform specialized functions to gather and prepare data in a format for detection system 130 to process in detecting events.

Capture agent 152 may have more or fewer subsystems and/or modules than shown in the figure, may combine two or more subsystems and/or modules, or may have a different configuration or arrangement of subsystems and/or modules. Subsystems and modules of capture agent 152 may be implemented in software (e.g., program code, instructions executable by a processor), in firmware, in hardware, or combinations thereof. The subsystems and/or modules of capture agent 152 may be implemented to perform techniques disclosed herein. In some embodiments, the software may be stored in a memory (e.g., a non-transitory computer-readable medium), on a memory device, or some other physical memory and may be executed by one or more processing units (e.g., one or more processors, one or more processor cores, one or more GPUs, etc.). Computer-executable instructions or firmware implementations of the processing unit(s) may include computer-executable or machine-executable instructions written in any suitable programming language to perform the various operations, functions, methods, and/or processes disclosed herein. Capture agent 152 may store or be implemented as program instructions that are loadable and executable on the processing unit(s), as well as data generated during the execution of these programs. The memory may be volatile (such as random access memory (RAM)) and/or non-volatile (such as read-only memory (ROM), flash memory, etc.). The memory may be implemented using any type of persistent storage device, such as computer-readable storage media. In some embodiments, computer-readable storage media may be configured to protect a computer from an electronic communication containing malicious code. The computer-readable storage media may include instructions stored thereon, that when executed on a processor, perform the operations disclosed herein.

In some embodiments, detection system 130 and user device 102 may be implemented using a computing system comprising one or more computers and/or servers that may include those described above. The computing system may be implemented as a cloud computing system. Detection system 130 and user device 102 may include several subsystems and/or modules, including some, which may not be shown. Detection system 130 may have more or fewer subsystems and/or modules than shown in the figure, may combine two or more subsystems and/or modules, or may have a different configuration or arrangement of subsystems and/or modules. Subsystems and modules of detection system 130 may be implemented in software (e.g., program code, instructions executable by a processor), in firmware, in hardware, or combinations thereof. The subsystems and/or modules of detection system 130 may be implemented to perform techniques disclosed herein. In some embodiments, the software may be stored in a memory (e.g., a non-transitory computer-readable medium), on a memory device, or some other physical memory and may be executed by one or more processing units (e.g., one or more processors, one or more processor cores, one or more GPUs, etc.). Computer-executable instructions or firmware implementations of the processing unit(s) may include computer-executable or machine-executable instructions written in any suitable programming language to perform the various operations, functions, methods, and/or processes disclosed herein. Detection system 130 may store program instructions that are loadable and executable on the processing unit(s), as well as data generated during the execution of these programs. The memory may be volatile (such as random access memory (RAM)) and/or non-volatile (such as read-only memory (ROM), flash memory, etc.). The memory may be implemented using any type of persistent storage device, such as computer-readable storage media. In some embodiments, computer-readable storage media may be configured to protect a computer from an electronic communication containing malicious code. The computer-readable storage media may include instructions stored thereon, that when executed on a processor, perform the operations disclosed herein.

Detection system 130, user device 102, and capture agent 152, individually or in combination, may provide other services and/or software applications in a virtual or non-virtual computing environment. For example, detection system 130 may be configured to run one or more of these services or software applications described in the foregoing disclosure. Such services may be offered on-demand to users of user device 102. Services may be facilitated or accessed by capture agent 152. In some embodiments, a specific instantiation of a service provided by detection system 130 may be referred to herein as a "service." Users operating user device 102 may use one or more applications to interact to utilize the services or applications provided by detection system 130. Services may be offered as a self-service or a subscription. Users can acquire the application services without the need for customers to purchase separate licenses and support. Examples of services may include a service provided under a Software as a Service (SaaS) model, a web-based service, an enterprise service, a cloud-based service, or some other service provided to user device 102 via network 170. A service made available to a user via network 170 (e.g., a communication network) from detection system 130 is referred to as a "cloud service." In some embodiments, detection system 130 may host an application, and a user may, via network 170, access the application at user device 102 on demand. Users operating user device 102 may in turn utilize one or more applications to interact with detection system 130 to utilize the services provided by subsystems and/or modules of detection system 130.

In some examples, a service may be an application service may be provided detection system 130 via a SaaS platform. The SaaS platform may be configured to provide services that fall under the SaaS category. The SaaS platform may manage and control the underlying software and infrastructure for providing the SaaS services. By utilizing the services provided by the SaaS platform, customers can utilize applications executing in detection system 130, which may be implemented as a cloud computing system. The cloud computing system may be implemented as a cloud-based infrastructure that is accessible via network 170. Various different SaaS services may be provided.

Detection system 130, user device 102, and capture agent 152 may each also include or be coupled to additional storage, which may be implemented using any type of persistent storage device, such as a memory storage device or other non-transitory computer-readable storage medium. In some embodiments, local storage may include or implement one or more databases (e.g., a document database, a relational database, or other type of database), one or more file stores, one or more file systems, or combinations thereof. For example, detection system 130 may be coupled to or may include one or more data stores. The data store(s) may store templates, edit scripts, and other information for the operations disclosed herein. The data store(s) may be implemented to store data using one or more data structures (e.g., a hash table). The data store(s) may be accessible to perform search and retrieval of data stored in the data store(s). The data store(s) may store data to perform event detection and to store information about detected events as disclosed herein. The memory and the additional storage are all examples of computer-readable storage media. For example, computer-readable storage media may include volatile or non-volatile, removable or non-removable media implemented in any method or technology for storage of information such as computer-readable instructions, data structures, program modules, or other data.

In at least one embodiment, a web session may begin with a user 103 on a web browser (e.g., application 150) initiating the browser request 110 for a document 156 from computer system 140. The user 103 may initiate the browser request 110 on a user device 102.

Once the computer system 140 has received the request, it may transmit a response 112 and return to the user device's 102 web browser 150. The response 112 of the computer system 140 may include the document 156 requested by the user 103. The computer system 140 may further include within the response 112 a Document Object Model (DOM), such as a hypertext markup language (HTML) DOM. The document 156 may be rendered according to the DOM. In one embodiment, the document 156 may contain a reference to the capture agent 152 (e.g., JavaScript code), which can then be fetched as a result from detection system 130. The capture agent 152 could also be sent separately from the document 156. Regardless, the capture agent 152 would be sent in conjunction with the document 156, such that the capture agent 152 can detect information about and operation of a website including the document 156. Being configured for communication with the detection system 130, the capture agent 152 can provide the detection system 130 with data detection of interaction with and operation of a website. Capture agent 152 can monitor interaction with a website via input to a client and can monitor operation of the website with respect to functions for displaying the website and/or communication with a host system hosting the website. As discussed below, detection system 130 operating with capture agent 152 can detect events related to operation of and/or interaction with a website to identify events that may cause to operation and/or performance of the website.

The capture agent 152, detection system 130, or a combination thereof may perform operations disclosed herein to detect events and to record information about those events. Information about events may be stored by the detection system, presented in a graphical interface at a client device/computer system, and/or communicated to another system, such as computer system 140 that provides documents for a website.

The processes and/or operations disclosed herein may be performed by capture agent 152, detection system 130, or a combination thereof. Capture agent 152 and detection system 130 may communicate with each other as part of performing event detection. Examples disclosed herein may be described as a process, which may be depicted as a flowchart, a flow diagram, a data flow diagram, a structure diagram, a sequence diagram, or a block diagram. Although such diagrams may describe operations as a sequential process, all or some of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function. Although some techniques may be described as being performed at one element of system 100, such as at user device 102 or detection system 130, the techniques may be performed in a variety of different combinations. For example, some or all of the features of detection system 130 may be implemented at a client device, or vice versa.

The processes disclosed herein may be implemented in software (e.g., code, instructions, program) executed by one or more processing units (e.g., processors cores), hardware, or combinations thereof. The software may be stored in a memory (e.g., on a memory device, on a non-transitory computer-readable storage medium). In some embodiments, the processes depicted in flowcharts herein can be implemented by one or more computer systems depicted in FIG. 1. The particular series of processing steps in this disclosure are not intended to be limiting. Other sequences of steps may also be performed according to alternative embodiments. For example, alternative embodiments of the present disclosure may perform the steps outlined above in a different order. Moreover, the individual steps illustrated in the figures may include multiple sub-steps that may be performed in various sequences as appropriate to the individual step. While processing disclosed herein may be described with respect to a single document, such processing may be performed for multiple documents. Furthermore, additional steps may be added or removed depending on the particular applications. One of ordinary skill in the art would recognize many variations, modifications, and alternatives.

In at least one embodiment, a system can include one or more processors and a memory accessible to the one or more processors, the memory comprising instructions that, when executed by the one or more processors, cause the one or more processors to perform operations disclosed herein. In at least one embodiment, a computer product is disclosed comprising a computer readable medium storing a plurality of instructions for controlling a computer system to perform an operation of any of the method disclosed herein. A system is disclosed herein including a computer product implementing any of the operations disclosed herein, and including one or more processors for executing instructions stored on the computer readable medium included in the computer product. In some embodiments, a system can include means for performing any of the methods disclosed herein. In some embodiments, a system can be configured to perform any of the methods disclosed herein. In at least one embodiment, a system can include modules that respectively perform the steps of any of the methods disclosed herein.

In an aspect of some embodiments, each process disclosed herein can be performed by one or more processing units. A processing unit may include one or more processors, including single core or multicore processors, one or more cores of processors, or combinations thereof. In some embodiments, a processing unit can include one or more special purpose co-processors such as graphics processors, digital signal processors (DSPs), or the like. In some embodiments, some or all of processing units can be implemented using customized circuits, such as application specific integrated circuits (ASICs), or field programmable gate arrays (FPGAs).

II. Webpage and Private Information Overview

In some embodiments, an application on a user device may generate a view of information, content, and/or resources, such as documents. For example, the application may be a web browser or a native application that communicates with a network computer (e.g., computer system 140). The view may be rendered based on one or more models. For example, a document may be rendered in the application, such as a web browser using a document object model (DOM). The view may be generated as an interface, e.g., a graphical user interface (GUI), based on a model. The document may be rendered in a view according to a format, e.g., a hypertext markup language (HTML) format. The interface for the view may be based on a structure or organization, such as a view hierarchy.

Figure 2:
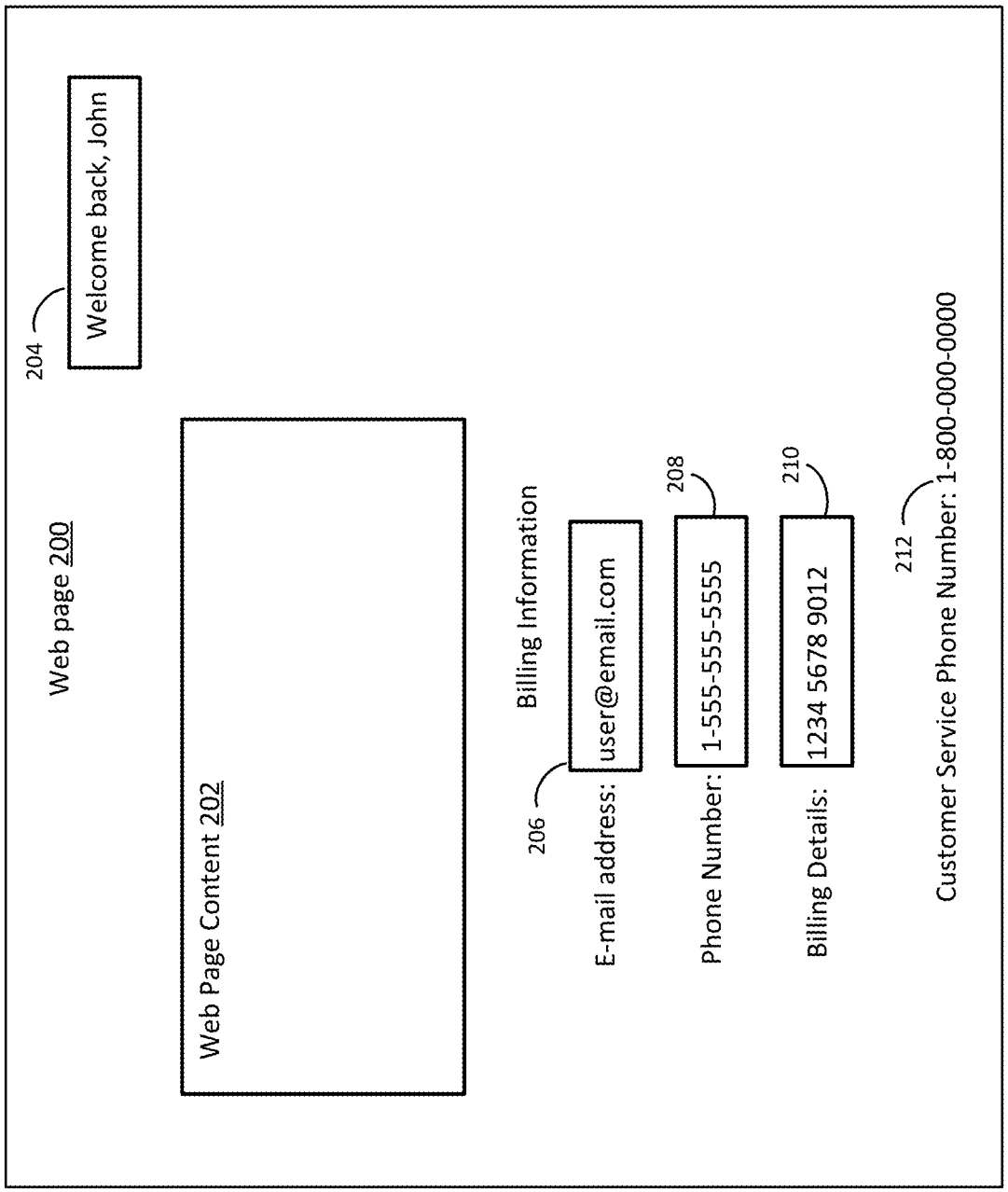
FIG. 2 illustrates an example web page, according to certain embodiments described herein.

FIG. 2 illustrates an example webpage 200, according to certain embodiments described herein. The webpage 200 can include an electronic document capable of being displayed and interacted with by a user device. The webpage 200 can include one of multiple web pages associated with a website such that a user can navigate across a number of web pages during a web session. The webpage 200 can be presented either on a native app (an application on a user device) or a web app (accessed through the web browser by typing in a URL, or via a bookmark or shortcut).

The webpage 200 can include various content, such as text, video, etc. For example, webpage content 202 can include a combination of text, images, interfaces to navigate the website, etc. The webpage content 202 can change across various web pages for the website.

Each webpage 200 can include various instances of private information. For example, responsive to logging into a portal associated with the website, a username 204 can be provided. The username 204 can be associated with metadata including private information, such as a username and password used to log into the portal.

In some embodiments, private information can be generated as a result of a server, e.g., which maintains the website, associating a logged-in user (e.g., a user account for the website being associated with a user device) with a user account. For example, responsive to a user signing up for a user account (e.g., by providing user details, a username, password), the server can associate the user device with the user account for subsequent network sessions (also referred to as subsequent web sessions). Accordingly, in some instances, upon starting a web session at a website, the server can associate the logged-in user with other previously-stored information about that user, which can then be displayed on the page back to the user (e.g., in username 204 on webpage 200). Further, a webpage illustrating user account details can include one or more fields containing private information relating to the user account.

Other instances of private information can be provided to a webpage 200 during a web session, such as an email address 206, phone number 208, and/or billing details 210. The instances of private information can be masked (e.g., removed, encrypted) from the stored user interactions with the website based on a type of private information. For instance, billing details 210 can be removed, while email address 206 and phone number 208 can be encrypted to allow for subsequent decryption in the event the user is to be contacted.

In some instances, the webpage 200 can include content that appears as private information but comprises information common across all web sessions. An example of such content includes a customer service phone number 212 comprising a phone number for an entity that is common across all web sessions. This can be referred to as a "false positive," as the content appears to include private information but can be prevented from being masked. Detecting such false positive content is described in greater detail with respect to FIG. 7.

III. Identification and Masking of Private Information in User Interactions with a Website As described above, a detection system can include a PII subsystem. The PII subsystem can be used to process session data and identify timestamps of instances of private information in the session data. The PII subsystem can further identify corresponding nodes in a DOM that correspond to the identified instances of private information. The corresponding nodes can be validated as comprising private information and the validated corresponding nodes can be passed to a capture agent for masking data associated with the validated corresponding nodes in subsequent web sessions.

A. PII Subsystem

Figure 3:
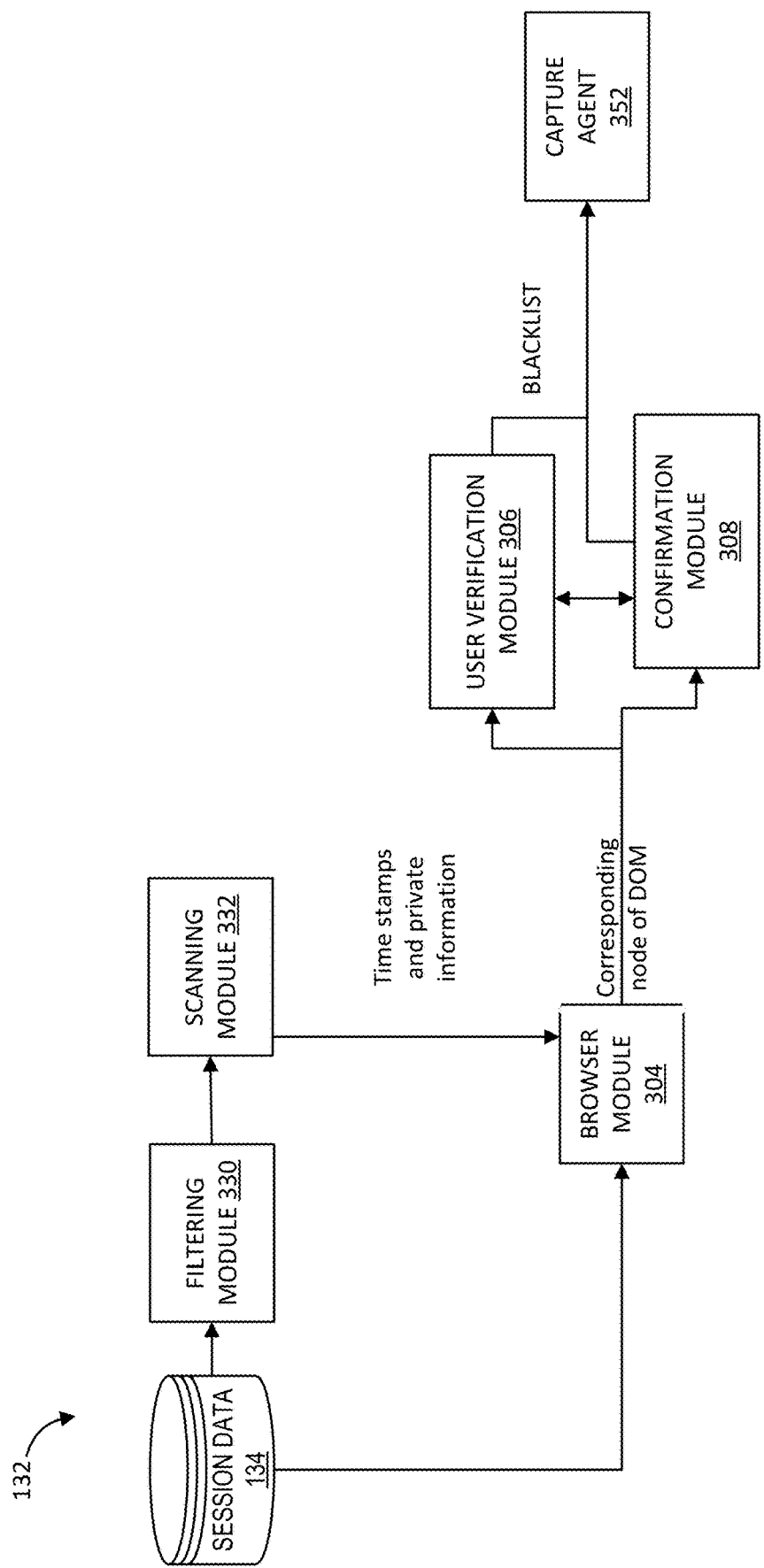
FIG. 3 is a block diagram of an example PII subsystem, according to certain embodiments described herein.

FIG. 3 is a block diagram of an example PII subsystem 132, according to certain embodiments described herein. PII subsystem 132 can include features similar to PII subsystem 132 described with respect to FIG. 1.

The PII subsystem 132 can include a scanning module 332. The scanning module 332 can analyze session data 134 and identify one or more pieces of private information in the session data 134, as well as identify the corresponding timestamps for when the private information occurred in the session. The session data 134 can include a series of user interactions (session events) with a website during a web session. The timestamps and private information can be passed from the scanning module 332 to a browser module 304, which can execute on a client device or other device of detection system 130. The PII subsystem 132 can filter the session data 134 using a filtering module 330 so that only data that is more likely to contain PII is sent to the scanning module 332. A browser module can correspond to a web browser or a native application.

The browser module 304 can load the sessions data 134, e.g., as might occur to replay the user interactions to an operator of a website to see how customers use the website. The browser module 304 may not need to have a display, but instead can just be the backend, although a display of the user interactions can be provided. Browser module 304 can identify, in session data 134, corresponding nodes in a DOM based on the obtained timestamps and private information from the scanning module 332. For instance, the browser module 304 can process the timestamps in relation to the DOM to identify a series of nodes that correspond to each instance of private information. The corresponding nodes identified by the browser module 304 can be provided to any of a user verification module 306 and a confirmation module 308.

Browser module 304 may or may not have a user interface. The browser module can browse the session data, which can be web session data or session data for native applications. Thus, browser module 304 can operate as a DOM parser. Such a DOM parser can parse DOM data into a structure that can be processed to identify corresponding nodes as described herein.

In some instances, after the browser module 304 is set to each assigned timestamp, each portion of corresponding text (e.g., text-based data) that includes private information can be used to locate a corresponding node on a webpage that contains the private information. In response to identifying a corresponding node, an identifier (e.g., a tag or label) can be created for each corresponding node for subsequent identification of each corresponding node.

In an embodiment, for a web-based application, browser module 304 can implement an index-based node identification process to identify corresponding nodes. For example, the index-based node identification process can use the parent/child architecture of a DOM to identify specific child nodes within the DOM that correlate with an identified instance of private information. For instance, an index sequence can specify 1-4-3-2 to indicate the identified node is the second node within the third node within the fourth node within the first node on the page.

In another embodiment, browser module 304 can include a DOM selection module. The DOM selection module can include a mechanism interacting with the DOM that identifies a node within the DOM based on an attribute of the node (e.g., a node identifier, a node name, CSS class, a combination of attributes and parent elements (e.g., body>header>user-name)). In this manner, the DOM selection module can identify a node even if there is a deviation in the ordering of nodes in the DOM.

In some embodiments, browser module 304 can analyze session data from a native application executing on the user device and translate a view of the DOM into an HTML structure. After translation, browser module 304 can use techniques as described herein to identify a corresponding node in the translated HTML structure and subsequently mask data on the user device responsive to identifying the corresponding node in the HTML structure. In other embodiments, the native application can use an original structure of a native view of the DOM to identify a corresponding node. For example, the native view can include user information with a first text view within a first container view, and a corresponding node can be identified by processing the native view.

In some instances, some native applications can include multiple instances of unique identifiers to identify individual view elements of the native application. The unique identifiers can be included within the captured session data for use in identifying private information within the tracked user interactions with the website.

The user verification module 306 can include a device associated with an administrator (e.g., of the website corresponding to the session data) capable of replaying web sessions and confirming any instances of private information identified by browser module 304. For instance, the user verification module 306 can view corresponding nodes and/or replay portions of a web session according to the timestamps in the web sessions. The user verification module 306 can validate each corresponding node as including private information.

In some instances, the user verification module 306 can identify a corresponding node as comprising a false positive instance of private information. In such instances, the corresponding node identified as comprising the false positive instance of private information can be ignored for subsequent/future web sessions.

In some embodiments, a notification specifying the corresponding node that comprises the private information and/or the timestamp indicating a time during the web session in which the private information is included can be provided to the user verification module 306. An administrator interacting with user verification module 306 can provide a confirmation of the corresponding node as comprising private information. For example, when browser module 304 identifies a node corresponding to the timestamp for private information, browser module 304 can provide a display of a page of the web session, highlighting the corresponding node (e.g., bolding a text box).

The confirmation module 308 similarly can confirm any instances of private information identified by browser module 304. As an example, the confirmation module 308 can determine whether a corresponding node satisfies specific criteria, such as whether the same node is identified to have PII in at least a threshold number of sessions. The corresponding nodes confirmed to include private information can be added to a blacklist and passed to a capture agent 352.

The capture agent 352 can mask data for each of the corresponding nodes in subsequent web sessions. For example, the capture agent 352 can be downloaded to a user device for masking of private information in subsequent web sessions with the website. In some instances, the capture agent 352 can be specific to a website (e.g., computer system 140). The capture agent 352 can obtain information for masking private information from a detection system 130 that can store session data and/or information for masking private information for any number of websites.

As mentioned above, the filtering module 330 may select certain session data 134 to be sent to the scanning module 332. Such filtering can address the problem of the amount of session data being too much for the scanning module 332 to analyze everything received from the captured user interactions. Thus, to be more efficient (e.g., faster) and use fewer computational resources (e.g., processing power and/or memory), there may be a filtering module 330 that selects only certain data for sending to the scanning module 332. This is done by filtering for data that is more likely to contain PII, so that effort is not wasted scanning user interaction data that does not include PII. Accordingly, the set of captured user interactions can be filtered using filtering module 330. The filtering module can determine which of the set of captured user interactions satisfy at least one criterion, thereby determining filtered user interactions. The filtered user interactions can be sent to scanning module 332.

Various criteria can be used to determine which user interaction data (e.g., based on which web page was being viewed by the user) should be sent to scanning module 332. When the session data 134 is received, the filtering module 330 can consider properties of the data to determine whether the data meets at least criterion for sending to scanning module 332. Filtering module 330 can store one or more criteria that can be checked against the priorities of each session or parts of a session to determine whether the corresponding session (user interaction) data should be sent to scanning module 332.

A property of the data can be determined in various ways. For example, a capture agent can identify one or more properties of a session, a page, or a particular user interaction, e.g., nodes of a document object model. A property of a session could be whether a particular page was viewed or whether input was provided on the page. The property can be provided in a predetermined segment of the session data, e.g., a category label as may be done in XML or other markup language. As another example, after receiving the session data (e.g., by detection system 130), a detection system can identify one or more properties. The detection system can use analysis across users for a website or across websites, e.g., by flagging whether a certain type of page was viewed.

Example properties of the data could include what page the user interaction data corresponds to or whether a particular page was visited during a session (e.g., a check-out page), at what time the page was accessed, number of page views across users in a given timeframe (e.g., a measurement interval such as minutes, hours, or days), user activity on the page (e.g., whether data was entered by the user on that page), number of interactions with a page in a given session, whether the page is flagged as containing PII, etc. The filtering module 330 can consider these properties and if, for example, a page is flagged as containing PII, it would meet the criteria and be sent to the scanning module 332. Alternatively, if a property of the data meets or exceeds a certain metric (e.g., number of page views across users in a given timeframe) then it would meet the criteria and be sent to the scanning module 332.

For example, if a user is on a checkout page on an e-commerce site, it is more likely that the user will enter PII on that page. Therefore, the page can be flagged as containing PII and session data 134 from that page can be sent to the scanning module 332 to be scanned for PII. Thus, as examples, filtering module 330 may have use any one or more criteria for this determination such as (1) number of page views; (2) engagement metrics; and/or (3) a customer-specified criterion.

As an example, an engagement metric may measure user interaction (e.g., user clicks or input data) on a page. A custom criterion may include information regarding property of the page, such as marking the page as asking the user to input a home address or credit card information. Another example of a custom criterion may include determining that session data 134 is to be sent to the scanning module 332 because the page had been flagged as prompting the user for their health insurance information. A custom criterion can be specified by including information in the website, so that such information is included in session data.

B. Example Method for Identifying and Masking Private Information

As noted above, the embodiments can provide systems and method for masking private information captured during user interactions with a website during a web session.

Figure 4:
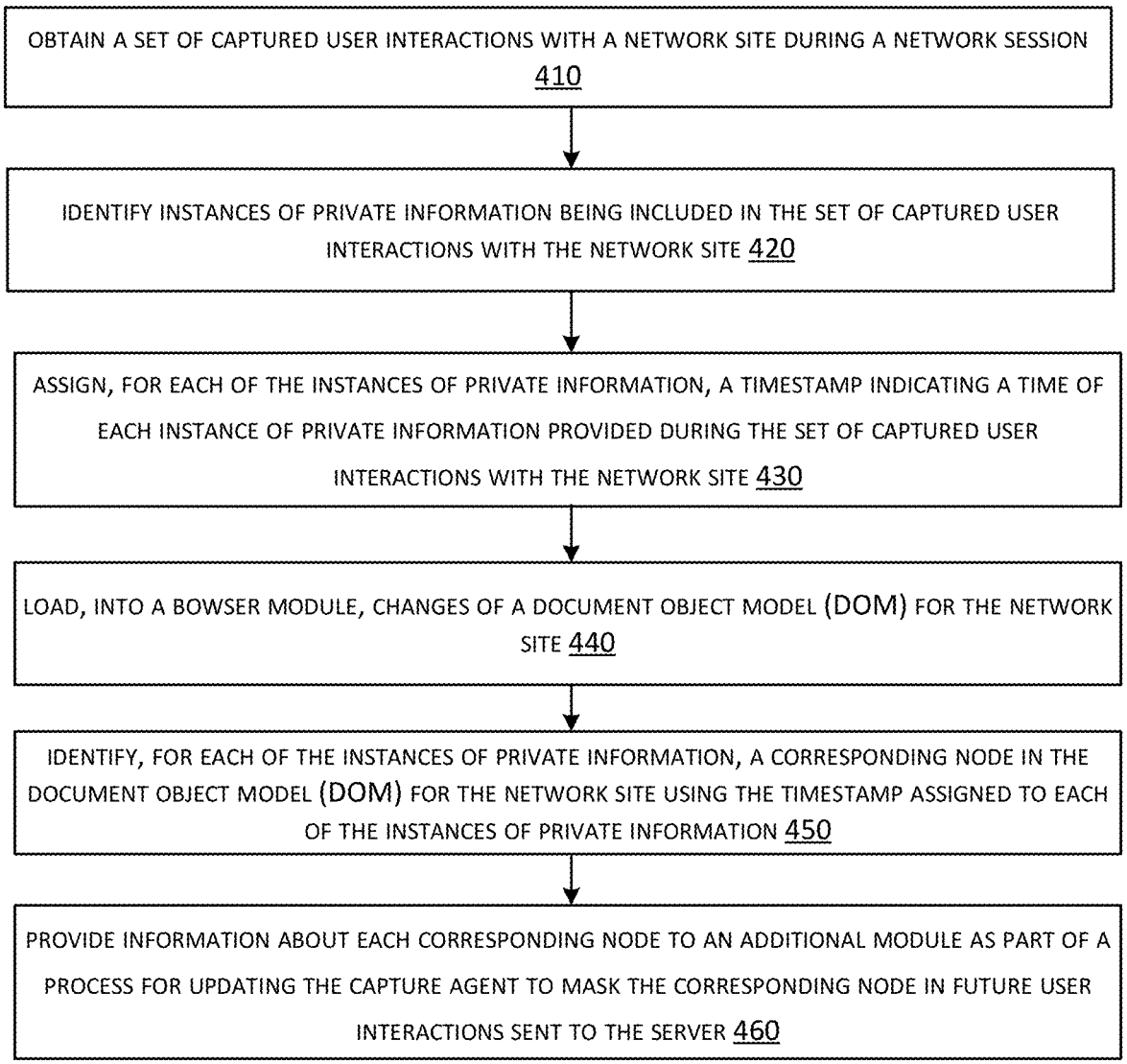
FIG. 4 is a flow diagram of a method for masking private information captured during user interactions with a website during a web session, according to certain embodiments described herein.

FIG. 4 is a flow diagram of a method for masking private information captured during user interactions with a network site during a network session (also referred to as a web session), according to certain embodiments described herein. The identification of private information can be performed by a PII subsystem 132 as described with respect to FIG. 3

At 410, the method can include obtaining a set of captured user interactions with the website during the web session. The set of captured user interactions include movements between portions of the website and/or data provided in one or more fields on the website. For instance, as a user interacts with a website during a web session, the interactions (e.g., mouse movements, a time that the user is interacting with each webpage, interfaces that the user interacts with, data provided in fields on the website) can be tracked and stored.

The tracked user interactions with the website during a web session can be stored such that the user interactions can be subsequently processed to derive insights into the website. For example, the stored user interactions can be replayed to identify points of frustration in the website or identify webpage(s) that led to the user abandoning the website.

At 420, the method can include identifying instances of private information being included in the set of captured user interactions with the website. Each instance of private information can include data (or corresponding metadata) provided in various fields of a website. For example, private information can include a user providing details (e.g., a user name, email address, phone number) requesting further information from an entity associated with the website. As another example, private information can include a user providing billing details (e.g., user name, address, primary account number for a payment device associated with the user) to complete a purchase on the website. As yet another example, private information can include information relating to a user account fetched from a server providing the website and displayed on a webpage.

The PII subsystem (e.g., 132) can be trained with multiple different categorized patterns of private information. The categorized patterns of private information can include multiple data patterns specific to different types of private information and a category of private information for each pattern. For example, a categorized pattern of private information can specify that a series of digits (e.g., 1-800-000-0000) can comprise a phone number and relates to a category for phone numbers. An output of the processed set of captured user interactions with the website can include each identified instance of private information and a category corresponding to each instance of private information.

The private information can be masked to mitigate unauthorized access to such information. For instance, a type of private information can be identified and a corresponding masking operation can be performed to mask the private information (e.g., encrypt the private information, remove the private information). Masking the private information can allow for processing of one or more tracked user interactions for replaying the web session and/or deriving insights into the website without leaving private information vulnerable to unauthorized access.

At 440, the method can include assigning a timestamp indicating a time of each instance of private information provided during the set of captured user interactions with the website for each of the instances of private information. A timestamp can specify a time during a web session that a user provided a corresponding instance of private information. Each timestamp can be used for identifying corresponding nodes in a DOM specific to the website or for replaying the web session.

At 440, the method can include loading changes of a document object model (DOM) for the website into a bowser module. For instance, the scanning module can load the changes to the DOM for the website into a browser module for subsequent masking of private information from the tracked user interactions. A DOM can include a series of nodes providing aspects of each web page that comprises a tree structure. Fields associated with each instance of private information identified during tracked user interactions can comprise a corresponding node in the DOM.

At 450, the method can include identifying a corresponding node in the DOM for the website using the timestamp assigned to each of the instances of private information. The scanning module can identify a corresponding node in the DOM for each of the identified instances of private information.

For instance, for each instance of private information, a webpage in which the private information was provided can be identified. In this example, the DOM structure can be processed to identify a portion of the DOM that correlates to the webpage. The identified portion of the DOM can then be processed to identify the node that corresponds to the field in which the instance of private information was provided.

Each identified node that corresponds with instances of private information can be identifiable in the DOM as fields that can include private information. For example, as subsequent tracked user interactions with the website are obtained, the instances of private information can be masked according to the corresponding nodes flagged in the DOM for the website. Further, as web sites change, the corresponding nodes for the website that include instances of private information can be modified to incorporate new fields that relate to the instance of private information.

At 460, the method can include providing information about each corresponding node to an additional module as part of a process for updating the capture agent to mask the corresponding node in future user interactions sent to the server. For example, the PII subsystem (e.g., 132) can provide corresponding nodes in the DOM that are validated (e.g., by a user verification module 306 and/or a confirmation module 308) to the capture agent 152. In some instances, the data for each corresponding node can be masked after a confirmation of the data as comprising private information. For example, the confirmation of the data comprising private information can include receiving a confirmation by a user verification module or determining that certain criteria is satisfied (e.g., the same node is identified to have PII in at least a threshold number of sessions).

In some instances, the additional module can include a device accessible to an administrator to obtain a notification of all fields of a website associated with private information, provide a link to view a screenshot of providing the private information into a corresponding field, or automatically update a black list of nodes that comprise private information. The additional module can also allow web session playback at a moment of private information presentation according to timestamps associated with each instance of private information.

The identified node (e.g., including a CSS tag) in the DOM can be provided in any notification to the administrator, e.g., to confirm the data really is private information. The administrator can then update the capture agent such that the identified node can be masked (e.g., encrypted or removed based on a type of private information). If certain criteria is satisfied (e.g., the same node is identified to have private information in at least a threshold number of sessions), information about the node can be added to the blacklist in the capture agent, so that the data is masked.

C. Masking Private Information

As noted above, instances of private information in tracked user interactions with a website can be masked. For instance, a capture agent (e.g., 152) can mask information included in corresponding nodes identified by a scanning module. Masking the private information can include removing the private information or encrypting the private information such that a secure device can subsequently decrypt the private information included in corresponding nodes.

A masking operation for a corresponding node (e.g., removal of private information, encryption of private information) can be based on a type of private information. Example types of private information can include user name, user contact information, billing details, etc. As a first example, a first set of private information types (e.g., billing details, user address information, passwords) may generally not be needed to be subsequently retrieved by any entity and can be removed from the session data. Accordingly, removing the private information can include removing the corresponding data from the user interactions or replacing the corresponding data with null values to prevent subsequent access to the private information. Accordingly, the masking operation can include a removal operation to remove private information.

Another masking operation can include encrypting private information. Encrypting private information can obfuscate the private information for subsequent processing of session data while also allowing secure access to the private information. For example, private information of a second set of private information types (e.g., user phone number, user email address) can be encrypted to allow for subsequent decryption by a secure device in the event the user is to be contacted. In this example, a device, such as a user verification module (e.g., 506), can include an encryption key that can decrypt the private information and access the private information.

D. Example Interactions Between Modules in the System for Identifying and Masking Private Information As noted above, modules included in a system (e.g., system 100 in FIG. 1) can interact to identify and mask private information as described herein. For instance, a detection system (e.g., 130), browser module (e.g., application 150), and user verification module (e.g., 306 in FIG. 3) can interact to process session data to identify instances of private information, identify corresponding nodes with each identified instance of private information, and confirm corresponding nodes as comprising private information.

Figure 5:
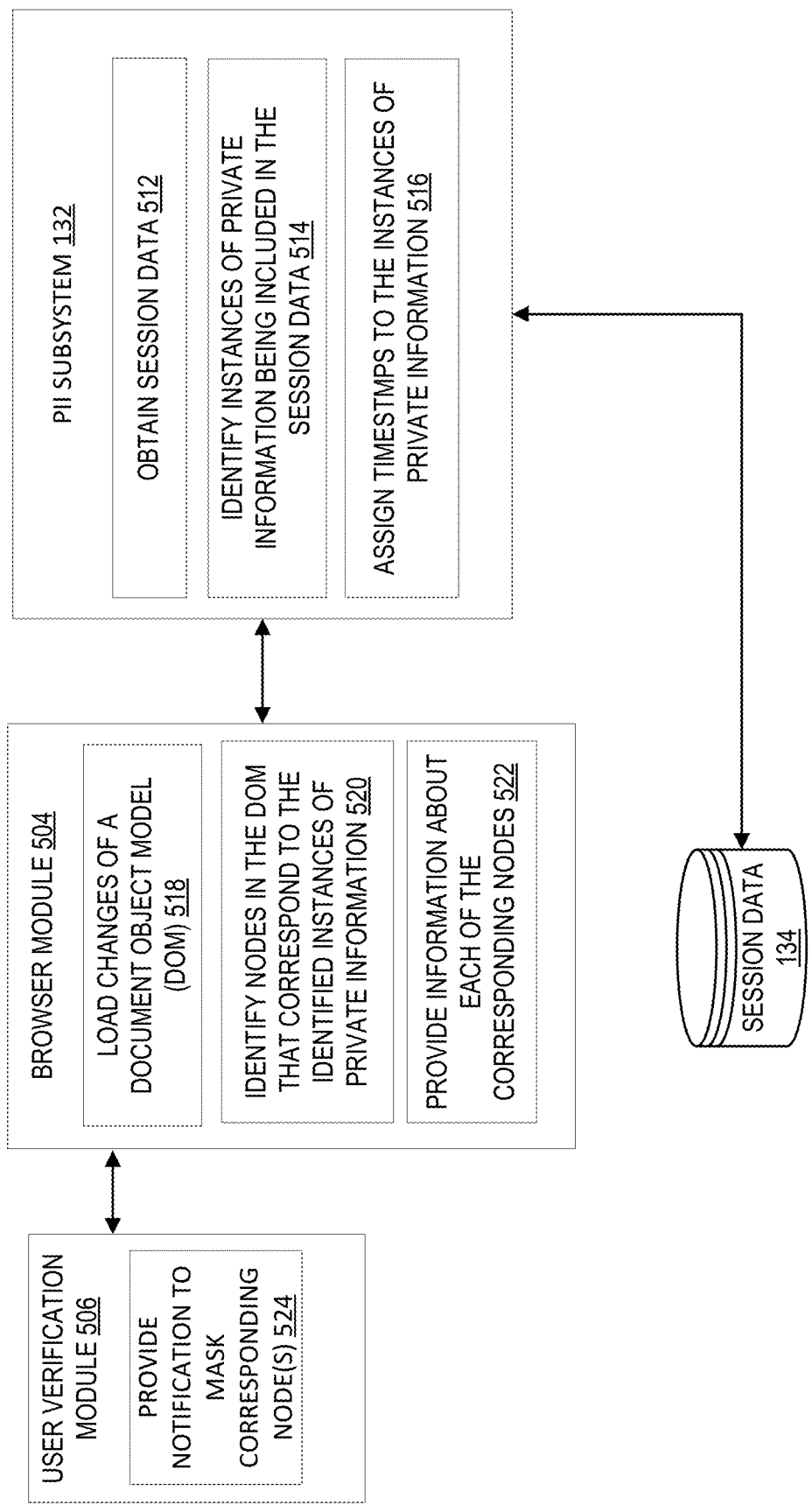
FIG. 5 is a block diagram illustrating an interaction between a scanning module, browser module, and a capture agent, according to certain embodiments described herein.

FIG. 5 is a block diagram 500 illustrating an interaction between a PII subsystem 132, browser module 504, and a capture agent 152, according to certain embodiments described herein. Browser module 504 can execute on a client device or any device of a detection system.

At 510, the capture agent(s) 152 can capture user interactions and mouse movements during a web session. The capture agent(s) 152 can track user interactions in a native application executing on a user device or on a web application during a web session. A web session can include a time duration in which a user interacts with the website. The web session can start when a user logs into a webpage and ends when the user leaves the webpage. All web pages accessed and all movements and times of the cursor on each webpage can be tracked during the website.

At 512, the PII subsystem 132 can receive the captured user interactions during the web session from the capture agent(s) 152. The tracked user interactions can specify webpages accessed, mouse movements, data provided in various fields provided in the website, etc.

At 514, the PII subsystem 132 can identify instances of private information provided during the web session. Example types of private information can include a user name, email address, phone number, address, payment device details, etc. In some instances, the private information can be included as metadata in a portion of the website. For example, as a user logs into an account on the website, the username and password for the account can be stored as metadata on the website.

At 516, the PII subsystem 132 can assign timestamps to each of the identified instances of private information. The timestamps can include a time during a web session in which the private information was provided on the webpage. The timestamps can be used for efficiently replaying the portions of the web session that includes the private information being included in the webpage.

At 518 changes of a DOM can be loaded to the browser module 504. The DOM can include a series of nodes comprising a tree structure providing the structure, content, and style of each webpage for the web site. The DOM can provide an object-oriented representation of the webpage such that the webpage can be efficiently modified. The changes to the DOM can include any changes to the DOM (e.g., changes made to a website). The changes can specify any modifications to the website to dynamically update nodes in the DOM to mask as described herein.

At 520, the browser module 504 can identify nodes in the DOM that correspond to the identified instances of private information. For instance, the PII subsystem 132 as described with respect to FIG. 3 can process the DOM to identify the corresponding nodes that relate to the instances of private information. In some instances, the PII subsystem 132 can retrieve previously-identified nodes that correspond to instances of private information for the website to identify any changes to the website or any newly-identified fields in which private information is provided.

At 522, the browser module 504 can provide information about each of the corresponding nodes to an additional module as part of a process for updating the capture agent to mask the corresponding nodes.

In some instances, each corresponding node identified by the PII subsystem 132 can be confirmed as including private information by a user verification module 506. User verification module 506 can obtain the information relating to the corresponding nodes from the browser module 504. The user verification module 506 can be used to review the tracked user interactions and perform various actions relating to the instances or private information, such as provide a confirmation to mask instances of private data, replay the web session, or decrypt any encrypted private information to securely access the private information.

Responsive to a determination that a corresponding node comprises private information or satisfies criteria identifying that the node comprises private information, the capture agent(s) can be instructed to mask data relating to the corresponding node.

At 524, the user verification module 506 can provide a notification to mask the corresponding node(s) to capture agent(s) 152. The notification can include a confirmation to mask specific nodes in a DOM or to prevent masking of a node (e.g., in the event of a false positive instance of private information). In some instances, responsive to masking the data for each corresponding node, the corresponding nodes can be flagged such that private information in subsequent web sessions can be efficiently masked and changes to the website can be dynamically modified to incorporate the changes to the website.

IV. Masking of Identified Instances of Private Information

As described above, instances of private information provided in tracked user interactions can be masked to mitigate unauthorized access of the private information. For instance, nodes in a DOM that correspond to instances of private information can be masked by capture agent(s) (e.g., 152) in future user interactions with a website. Masking the private information can allow for subsequent processing of session data (e.g., data comprising multiple web sessions with a website) and deriving insight into the session data while mitigating unauthorized access to private information included in the session data.

A. Example Process for Masking Instances of Private Information

Identified instances of private information can be masked in subsequent web sessions to mitigate unauthorized access to such private information. For instance, a capture agent can either encrypt or remove data associated with corresponding nodes identified from session data by the PII subsystem. In the process of identifying the private information, the detection system can determine the type of private information in a node. Then, the updated capture agent corresponding to a given server (e.g., a website that might be hosed on computer system 140) can be sent to a user device, so that it can mask different data in a suitable manner.

Figure 6:
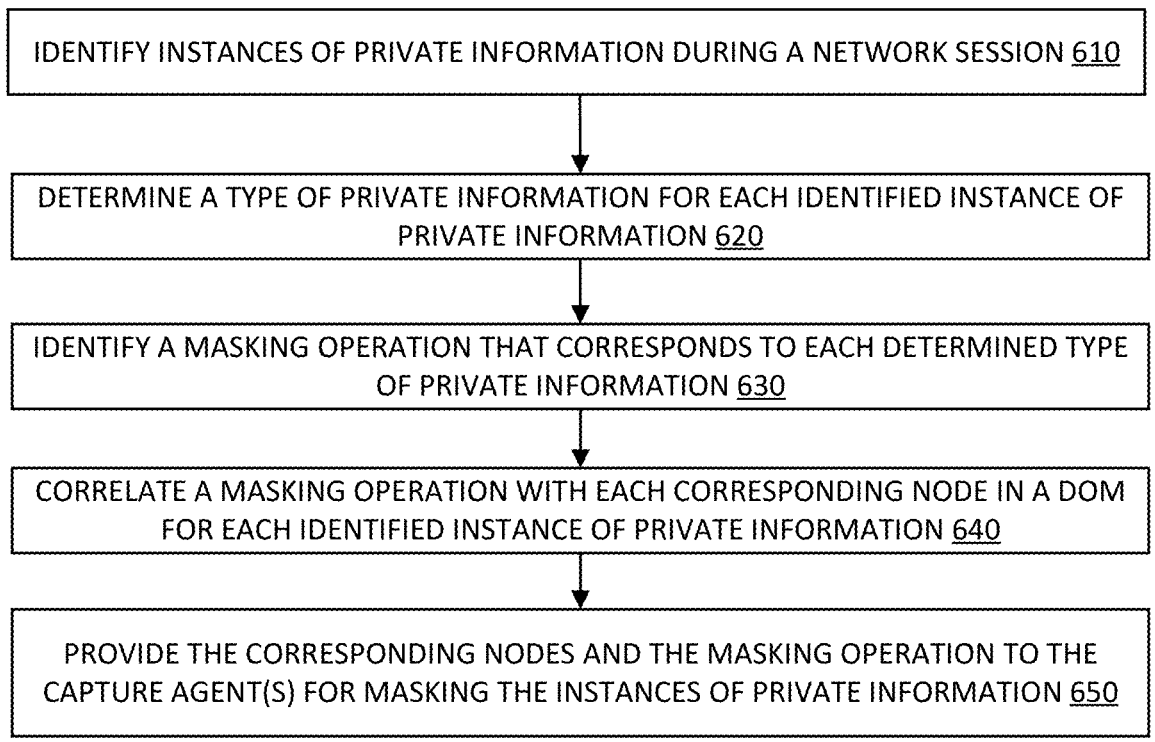
FIG. 6 is a flow process illustrating a process for masking identified instances of private information, according to certain embodiments described herein.

FIG. 6 is a flow process 600 illustrating an example process for masking identified instances of private information, according to certain embodiments described herein.

At 610, the process can include identifying (e.g., by PII subsystem (e.g., 132) as described in FIG. 3) instances of private information during a network session (also referred to as a web session). For example, the tracked user interactions can be processed to identify any private information being provided during the web session. This can include processing all text provided to the website during the website and identifying any text including content that includes private information.

At 620, the process can include determining a type of private information for each identified instance of private information. Each type of private information can be based on a content specific to each type of information, such as a name, address, phone number, billing details, etc. For instance, as a phone number generally comprises a series of numerical digits, a first instance of private information comprising a similar series of digits (e.g., a specific number or one of a set of numbers) can be identified as a phone number. This can be repeated for each instance of private information. Each type of private information can have a certain template (e.g., pattern of numbers and/or letters) to which a given instance can be compared to determine the type of private data.

At 630, the process can include identifying a masking operation that corresponds to each determined type of private information. The masking operation can include an operation to be performed based on a type of private information. Example masking operations can include encrypting data or removing data from a corresponding node. Private information can be encrypted if the type of data (e.g., phone number, email address) may be used for an administrator to contact a user, for example. Accordingly, the masking operation can includes an encryption operation to encrypt private information such that the encrypted private information can be subsequently decrypted to securely access the private information. Other types of private information that can be encrypted can include private information relating to targeting marketing materials to a user or looking up other sessions for a user providing insights into user interactions with a website. Additionally, private information can be removed if the type of data (e.g., payment device details) are generally not needed for any future use by an administrator. Each type of private information can be associated with a corresponding masking operation.

At 640, the process can include correlating a masking operation with each node in a DOM that is identified as including private information. For instance, along with an identifier for each node corresponding to private information, a field or a pointer an indication to either encrypt or mask the data included in each corresponding node. The encrypted data can be decrypted using a key accessible only by a secure source (e.g., a user verification module). The identifier (e.g., a particular tag or node identifier in a DOM tree) and the field/pointer of the masking operation can be used later by a capture agent, e.g., after it is updated.

At 660, the process can include providing the corresponding nodes and the masking operation to the capture agent(s) for masking the instances of private information. Accordingly, the capture agent can be updated with an indication (e.g., a field or pointer) indicating that data relating to a specific corresponding node is to be masked using a specific masking operation. The indication can be added to the blacklist indicating which masking operation the capture agent is to use to mask corresponding data for subsequent web sessions. The user device executing the capture agent(s) can then mask the instances of private information according to the masking operation associated with each instance of private information.

B. Identifying False Positive Instances of Private Information

As noted above, in some instances, false positive instances of private information can be identified. An example of a false positive instance of private information can include a customer service phone number displayed on the network site (also referred to as a website). In such instances, the masking of the false positive instances can be prevented to increase efficiency in masking only private information.

Figure 7:
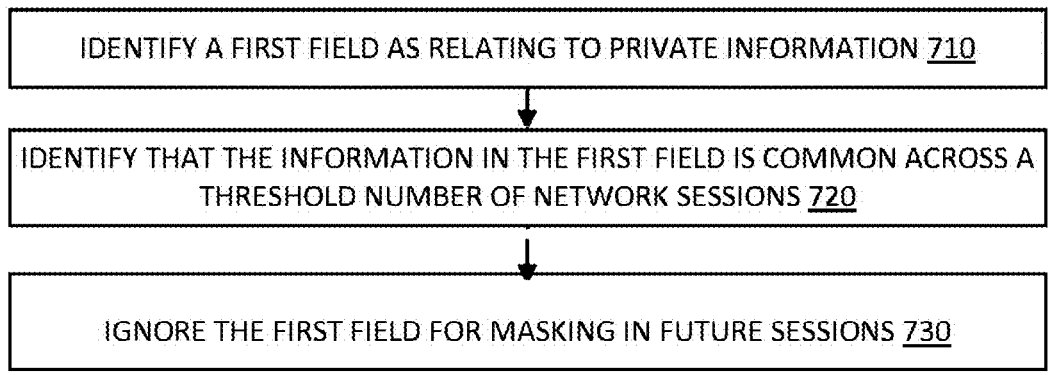
FIG. 7 is a flow diagram illustrating a process for identifying a false positive instance of private information, according to certain embodiments described herein.

FIG. 7 is a flow diagram illustrating a process 700 for identifying a false positive instance of private information, according to certain embodiments described herein.

At 710, the PII subsystem (e.g., 132) can identify a first field as relating to private information. For instance, the first field can include a customer service phone number or a customer service email address for an entity associated with the website. The first field can be common across multiple web sessions.

At 720, the PII subsystem (e.g., 132) can identify that information in the first field is common across a threshold number of web sessions. As an example, if the specific data included in the first field (e.g., a 1-800 phone number) is included in a threshold number of previous (or current) web sessions, the first field may not include private information, but rather, publicly-accessible information displayed on the website. For example, if five concurrent sessions each identify a same phone number, it can be assumed that a single user is not active in different concurrent sessions and that the phone number does not comprise private information.

As private information (e.g., a username, email address) generally is unique for each user, private information generally is not common across multiple tracked user interactions with the website. Accordingly, if the information in the first field is common (e.g., comprising the same phone number), the information may not comprise private data, but rather, publicly-accessible data for an entity associated with the website. In some instances, a scanning module in the PII subsystem can identify whether a corresponding field relating to the first field has been previously identified as a false positive instance of private information.

At 730, the PII subsystem (e.g., 132) can be taught to ignore false positive private information relating to the first field in subsequent/future web sessions. For example, an instruction can be provided to a scanning module (e.g., 332) to ignore false positive PII text in subsequent web sessions. Responsive to determining that information in the first field is common across a threshold number of web session (e.g., a phone number is common across a threshold number of concurrent web sessions), that false positive instance of private information can be ignored and not included in a blacklist as described herein.

V. Example Computer System

Figure 8:
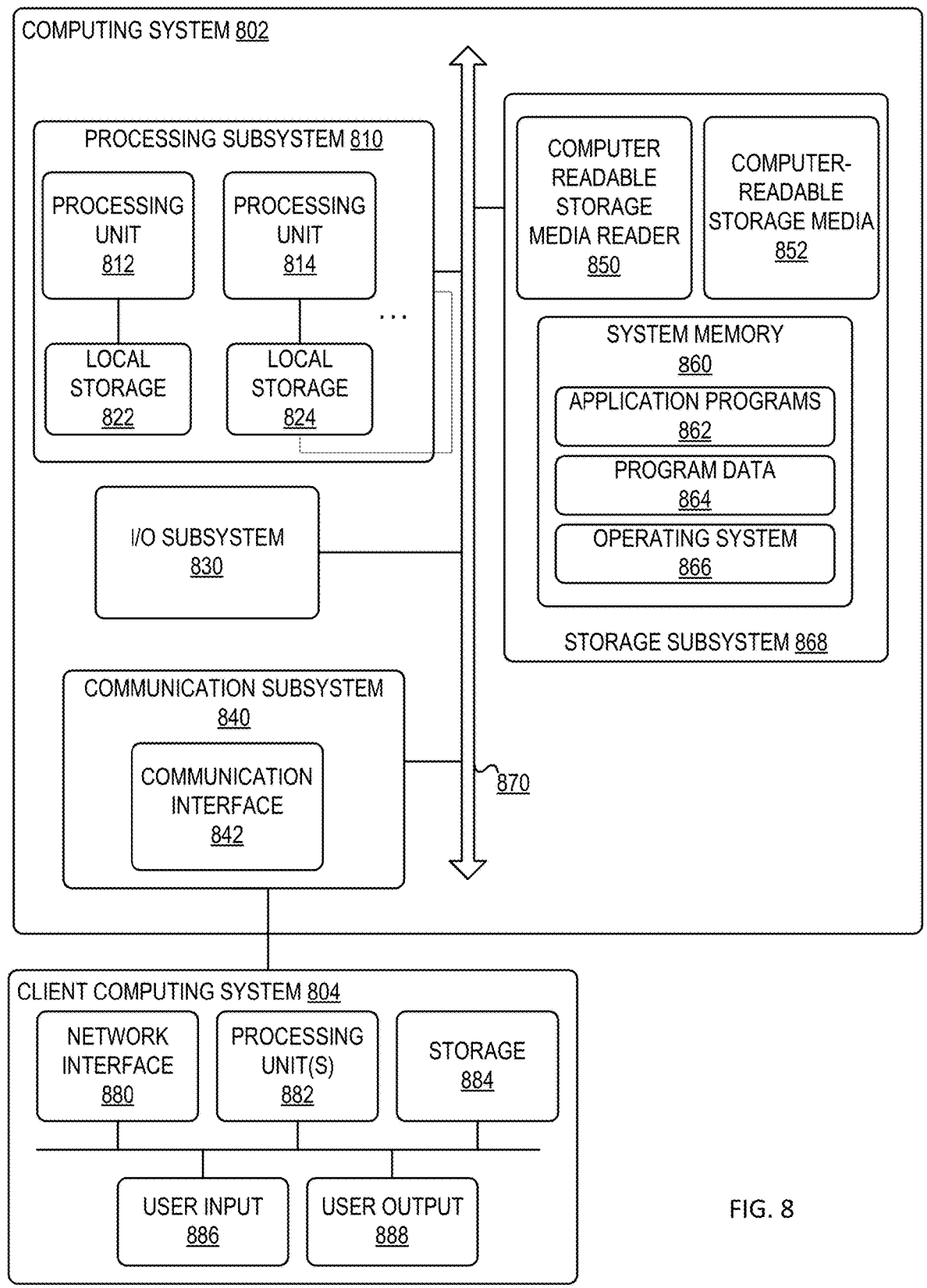
FIG. 8 illustrates an example of a computing system that may be used with certain embodiments described herein.

Various operations described herein may be implemented on computer systems, which may be of generally conventional design. FIG. 8 shows a simplified block diagram of a representative computing system 802 and client computing system 804 usable to implement certain embodiments of the present disclosure. In various embodiments, computing system 802 or similar systems may implement capture management system, or any other computing system described herein or portions thereof.

Computing system 802 may be one of various types, including a handheld portable device (e.g., an iPhone® cellular phone, an iPad® computing tablet, a PDA), a wearable device (e.g., a Google Glass® head mounted display), a personal computer, a workstation, a mainframe, a kiosk, a server rack, or any other data processing system.

Computing system 802 may include processing subsystem 810. Processing subsystem 810 may communicate with a number of peripheral systems via bus subsystem 870. These peripheral systems may include I/O subsystem 830, storage subsystem 868, and communication subsystem 840.

Bus subsystem 870 provides a mechanism for letting the various components and subsystems of computing system 802 communicate with each other as intended. Although bus subsystem 870 is shown schematically as a single bus, alternative embodiments of the bus subsystem may utilize multiple buses. Bus subsystem 870 may form a local area network that supports communication in processing subsystem 810 and other components of server computing system 820. Bus subsystem 870 may be implemented using various technologies including server racks, hubs, routers, etc. Bus subsystem 870 may be any of several types of bus structures including a memory bus or memory controller, a peripheral bus, and a local bus using any of a variety of bus architectures. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which may be implemented as a Mezzanine bus manufactured to the IEEE P1386.1 standard, and the like.

I/O subsystem 830 may include devices and mechanisms for inputting information to computing system 802 and/or for outputting information from or via computing system 802. In general, use of the term "input device" is intended to include all possible types of devices and mechanisms for inputting information to computing system 802. User interface input devices may include, for example, a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may also include motion sensing and/or gesture recognition devices such as the Microsoft Kinect® motion sensor that enables users to control and interact with an input device, the Microsoft Xbox® 360 game controller, devices that provide an interface for receiving input using gestures and spoken commands. User interface input devices may also include eye gesture recognition devices such as the Google Glass® blink detector that detects eye activity (e.g., "blinking" while taking pictures and/or making a menu selection) from users and transforms the eye gestures as input into an input device (e.g., Google Glass®). Additionally, user interface input devices may include voice recognition sensing devices that enable users to interact with voice recognition systems (e.g., Siri® navigator), through voice commands.

Other examples of user interface input devices include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, medical ultrasonography devices. User interface input devices may also include, for example, audio input devices such as MIDI keyboards, digital musical instruments and the like.

User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. In general, use of the term "output device" is intended to include all possible types of devices and mechanisms for outputting information from computing system 802 to a user or other computer. For example, user interface output devices may include, without limitation, a variety of display devices that visually convey text, graphics and audio/video information such as monitors, printers, speakers, headphones, automotive navigation systems, plotters, voice output devices, and modems.

Processing subsystem 810 controls the operation of computing system 802 and may comprise one or more processing units 812, 814, etc. A processing unit may include one or more processors, including single core processor or multicore processors, one or more cores of processors, or combinations thereof. In some embodiments, processing subsystem 810 may include one or more special purpose co-processors such as graphics processors, digital signal processors (DSPs), or the like. In some embodiments, some or all of the processing units of processing subsystem 810 may be implemented using customized circuits, such as application specific integrated circuits (ASICs), or field programmable gate arrays (FPGAs). In some embodiments, such integrated circuits execute instructions that are stored on the circuit itself. In other embodiments, processing unit(s) may execute instructions stored in local storage, e.g., local storage 822, 824. Any type of processors in any combination may be included in processing unit(s) 812, 814.

In some embodiments, processing subsystem 810 may be implemented in a modular design that incorporates any number of modules (e.g., blades in a blade server implementation). Each module may include processing unit(s) and local storage. For example, processing subsystem 810 may include processing unit 812 and corresponding local storage 822, and processing unit 814 and corresponding local storage 824.

Local storage 822, 824 may include volatile storage media (e.g., conventional DRAM, SRAM, SDRAM, or the like) and/or non-volatile storage media (e.g., magnetic or optical disk, flash memory, or the like). Storage media incorporated in local storage 822, 824 may be fixed, removable or upgradeable as desired. Local storage 822, 824 may be physically or logically divided into various subunits such as a system memory, a ROM, and a permanent storage device. The system memory may be a read-and-write memory device or a volatile read-and-write memory, such as dynamic random access memory. The system memory may store some or all of the instructions and data that processing unit(s) 812, 814 need at runtime. The ROM may store static data and instructions that are needed by processing unit(s) 812, 814. The permanent storage device may be a non-volatile read-and-write memory device that may store instructions and data even when a module including one or more processing units 812, 814 and local storage 822, 824 is powered down. The term "storage medium" as used herein includes any medium in which data may be stored indefinitely (subject to overwriting, electrical disturbance, power loss, or the like) and does not include carrier waves and transitory electronic signals propagating wirelessly or over wired connections.

In some embodiments, local storage 822, 824 may store one or more software programs to be executed by processing unit(s) 812, 814, such as an operating system and/or programs implementing various server functions such as functions of capture management system, or any other server(s) associated with capture management system. "Software" refers generally to sequences of instructions that, when executed by processing unit(s) 812, 814 cause computing system 802 (or portions thereof) to perform various operations, thus defining one or more specific machine implementations that execute and perform the operations of the software programs. The instructions may be stored as firmware residing in read-only memory and/or program code stored in non-volatile storage media that may be read into volatile working memory for execution by processing unit(s) 812, 814. In some embodiments the instructions may be stored by storage subsystem 868 (e.g., computer readable storage media). In various embodiments, the processing units may execute a variety of programs or code instructions and may maintain multiple concurrently executing programs or processes. At any given time, some or all of the program code to be executed may be resident in local storage 822, 824 and/or in storage subsystem including potentially on one or more storage devices. Software may be implemented as a single program or a collection of separate programs or program modules that interact as desired. From local storage 822, 824 (or non-local storage described below), processing unit(s) 812, 814 may retrieve program instructions to execute and data to process in order to execute various operations described above.

Storage subsystem 868 provides a repository or data store for storing information that is used by computing system 802. Storage subsystem 868 provides a tangible non-transitory computer-readable storage medium for storing the basic programming and data constructs that provide the functionality of some embodiments. Software (programs, code modules, instructions) that when executed by processing subsystem 810 provide the functionality described above may be stored in storage subsystem 868. The software may be executed by one or more processing units of processing subsystem 810. Storage subsystem 868 may also provide a repository for storing data used in accordance with the present disclosure.

Storage subsystem 868 may include one or more non-transitory memory devices, including volatile and non-volatile memory devices. As shown in FIG. 8, storage subsystem 868 includes a system memory 860 and a computer-readable storage media 852. System memory 860 may include a number of memories including a volatile main RAM for storage of instructions and data during program execution and a non-volatile ROM or flash memory in which fixed instructions are stored. In some implementations, a basic input/output system (BIOS), containing the basic routines that help to transfer information between elements within computing system 802, such as during start-up, may typically be stored in the ROM. The RAM typically contains data and/or program modules that are presently being operated and executed by processing subsystem 810. In some implementations, system memory 860 may include multiple different types of memory, such as static random access memory (SRAM) or dynamic random access memory (DRAM). Storage subsystem 868 may be based on magnetic, optical, semiconductor, or other data storage media. Direct attached storage, storage area networks, network-attached storage, and the like may be used. Any data stores or other collections of data described herein as being produced, consumed, or maintained by a service or server may be stored in storage subsystem 868.

By way of example, and not limitation, as depicted in FIG. 8, system memory 860 may store application programs 862, which may include client applications, Web browsers, mid-tier applications, relational database management systems (RDBMS), etc., program data 864, and one or more operating systems 866. By way of example, an example operating systems may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® 10 OS, and Palm® OS operating systems.

Computer-readable storage media 852 may store programming and data constructs that provide the functionality of some embodiments. Software (programs, code modules, instructions) that when executed by processing subsystem 810 a processor provide the functionality described above may be stored in storage subsystem 868. By way of example, computer-readable storage media 852 may include non-volatile memory such as a hard disk drive, a magnetic disk drive, an optical disk drive such as a CD ROM, DVD, a Blu-Ray® disk, or other optical media. Computer-readable storage media 852 may include, but is not limited to, Zip® drives, flash memory cards, universal serial bus (USB) flash drives, secure digital (SD) cards, DVD disks, digital video tape, and the like. Computer-readable storage media 852 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. Computer-readable storage media 852 may provide storage of computer-readable instructions, data structures, program modules, and other data for computing system 802.

In certain embodiments, storage subsystem 868 may also include a computer-readable storage media reader 850 that may further be connected to computer-readable storage media 852. Together and, optionally, in combination with system memory 860, computer-readable storage media 852 may comprehensively represent remote, local, fixed, and/or removable storage devices plus storage media for storing computer-readable information.

In certain embodiments, computing system 802 may provide support for executing one or more virtual machines. Computing system 802 may execute a program such as a hypervisor for facilitating the configuring and managing of the virtual machines. Each virtual machine may be allocated memory, compute (e.g., processors, cores), I/O, and networking resources. Each virtual machine typically runs its own operating system, which may be the same as or different from the operating systems executed by other virtual machines executed by computing system 802. Accordingly, multiple operating systems may potentially be run concurrently by computing system 802. Each virtual machine generally runs independently of the other virtual machines.

Communication subsystem 840 provides an interface to other computer systems and networks. Communication subsystem 840 serves as an interface for receiving data from and transmitting data to other systems from computing system 802. For example, communication subsystem 840 may enable computing system 802 to establish a communication channel to one or more client computing devices via the Internet for receiving and sending information from and to the client computing devices.

Communication subsystem 840 may support both wired and/or wireless communication protocols. For example, in certain embodiments, communication subsystem 840 may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components. In some embodiments, communication subsystem 840 may provide wired network connectivity (e.g., Ethernet) in addition to or instead of a wireless interface.

Communication subsystem 840 may receive and transmit data in various forms. For example, in some embodiments, communication subsystem 840 may receive input communication in the form of structured and/or unstructured data feeds, event streams, event updates, and the like. For example, communication subsystem 840 may be configured to receive (or send) data feeds in real-time from users of social media networks and/or other communication services such as Twitter® feeds, Facebook® updates, web feeds such as Rich Site Summary (RSS) feeds, and/or real-time updates from one or more third party information sources.

In certain embodiments, communication subsystem 840 may be configured to receive data in the form of continuous data streams, which may include event streams of real-time events and/or event updates, that may be continuous or unbounded in nature with no explicit end. Examples of applications that generate continuous data may include, for example, sensor data applications, financial tickers, network performance measuring tools (e.g. network monitoring and traffic management applications), clickstream analysis tools, automobile traffic monitoring, and the like.

Communication subsystem 840 may also be configured to output the structured and/or unstructured data feeds, event streams, event updates, and the like to one or more databases that may be in communication with one or more streaming data source computers coupled to computing system 802.

Communication subsystem 840 may provide a communication interface 842, e.g., a WAN interface, which may provide data communication capability between the local area network (bus subsystem 870) and a larger network, such as the Internet. Conventional or other communications technologies may be used, including wired (e.g., Ethernet, IEEE 802.3 standards) and/or wireless technologies (e.g., Wi-Fi, IEEE 802.11 standards).

Computing system 802 may operate in response to requests received via communication interface 842. Further, in some embodiments, communication interface 842 may connect computing systems 802 to each other, providing scalable systems capable of managing high volumes of activity. Conventional or other techniques for managing server systems and server farms (collections of server systems that cooperate) may be used, including dynamic resource allocation and reallocation.

Computing system 802 may interact with various user-owned or user-operated devices via a wide-area network such as the Internet. An example of a user-operated device is shown in FIG. 8 as client computing system 804. Client computing system 804 may be implemented, for example, as a consumer device such as a smart phone, other mobile phone, tablet computer, wearable computing device (e.g., smart watch, eyeglasses), desktop computer, laptop computer, and so on.

For example, client computing system 804 may communicate with computing system 802 via communication interface 842. Client computing system 804 may include conventional computer components such as processing unit(s) 882, storage device 884, network interface 880, user input device 886, and user output device 888. Client computing system 804 may be a computing device implemented in a variety of form factors, such as a desktop computer, laptop computer, tablet computer, smart phone, other mobile computing device, wearable computing device, or the like.

Processing unit(s) 882 and storage device 884 may be similar to processing unit(s) 812, 814 and local storage 822, 824 described above. Suitable devices may be selected based on the demands to be placed on client computing system 804; for example, client computing system 804 may be implemented as a "thin" client with limited processing capability or as a high-powered computing device. Client computing system 804 may be provisioned with program code executable by processing unit(s) 882 to enable various interactions with computing system 802 of a message management service such as accessing messages, performing actions on messages, and other interactions described above. Some client computing systems 804 may also interact with a messaging service independently of the message management service.

Network interface 880 may provide a connection to a wide area network (e.g., the Internet) to which communication interface 842 of computing system 802 is also connected. In various embodiments, network interface 880 may include a wired interface (e.g., Ethernet) and/or a wireless interface implementing various RF data communication standards such as Wi-Fi, Bluetooth, or cellular data network standards (e.g., 3G, 4G, LTE, etc.).

User input device 886 may include any device (or devices) via which a user may provide signals to client computing system; client computing system may interpret the signals as indicative of particular user requests or information. In various embodiments, user input device 886 may include any or all of a keyboard, touch pad, touch screen, mouse or other pointing device, scroll wheel, click wheel, dial, button, switch, keypad, microphone, and so on.

User output device 888 may include any device via which client computing system may provide information to a user. For example, user output device 888 may include a display to display images generated by or delivered to client computing system 804. The display may incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). Some embodiments may include a device such as a touchscreen that function as both input and output device. In some embodiments, other user output devices 888 may be provided in addition to or instead of a display. Examples include indicator lights, speakers, tactile "display" devices, printers, and so on.

Some embodiments include electronic components, such as microprocessors, storage and memory that store computer program instructions in a computer readable storage medium. Many of the features described in this specification may be implemented as processes that are specified as a set of program instructions encoded on a computer readable storage medium. When these program instructions are executed by one or more processing units, they cause the processing unit(s) to perform various operation indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 812, 814 and 882 may provide various functionality for computing system 802 and client computing system, including any of the functionality described herein as being performed by a server or client, or other functionality associated with message management services.

It will be appreciated that computing system 802 and client computing system 804 are illustrative and that variations and modifications are possible. Computer systems used in connection with embodiments of the present disclosure may have other capabilities not specifically described here. Further, while computing system 802 and client computing system 1204 are described with reference to particular blocks, it is to be understood that these blocks are defined for convenience of description and are not intended to imply a particular physical arrangement of component parts. For instance, different blocks may be but need not be located in the same facility, in the same server rack, or on the same motherboard. Further, the blocks need not correspond to physically distinct components. Blocks may be configured to perform various operations, e.g., by programming a processor or providing appropriate control circuitry, and various blocks might or might not be reconfigurable depending on how the initial configuration is obtained. Embodiments of the present disclosure may be realized in a variety of apparatus including electronic devices implemented using any combination of circuitry and software.

While this disclosure has been described with respect to specific embodiments, one skilled in the art will recognize that numerous modifications are possible. For instance, although specific processes are described with reference to FIG. 1, other processes may be implemented. Embodiments of this disclosure may be realized using a variety of computer systems and communication technologies including but not limited to specific examples described herein.

In the detailed description of exemplary embodiments of this disclosure, reference is made to the accompanying drawings which form a part hereof, and in which is shown by way of illustration specific exemplary embodiments in which this disclosure may be practiced. These embodiments are described in sufficient detail to enable those skilled in the art to practice this disclosure, and it is to be understood that other embodiments may be utilized and that logical, mechanical, electrical and other changes may be made without departing from the scope of the present disclosure.

Embodiments of the present disclosure may be realized using any combination of dedicated components and/or programmable processors and/or other programmable devices. The various processes described herein may be implemented on the same processor or different processors in any combination. Where components are described as being configured to perform certain operations, such configuration may be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

It is apparent for those skilled in the art that, for the particular operation processes of the units described above, reference may be made to the corresponding steps/components in the related method/system embodiment sharing the same concept and the reference is regarded as the disclosure of the related units too. And therefore some of the particular operation processed will not be described repeatedly or in detail for concision of the description.

It should be understood that any of the embodiments of the present disclosure can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional, functional, and/or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present disclosure may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer apparatus may include a monitor, printer, or other suitable display for providing any of the results mentioned herein to a user.

Any of the methods disclosed herein may be totally or partially performed with a computer system including one or more processors, which can be configured to perform the steps. Thus, embodiments can be directed to computer systems configured to perform the steps of any of the methods disclosed herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The features and advantages described in the detailed description are not all inclusive and, in particular, many additional features and advantages will be apparent to one of ordinary skill in the art in view of the drawings, detailed description, and claims. Moreover, it should be noted that the language used in the detailed description has been principally selected for readability and instructional purposes, and may not have been selected to delineate or circumscribe the inventive subject matter.

Note that in this description, references to "one embodiment," "an embodiment" or "some embodiments" mean that the feature being referred to is included in at least one embodiment of this disclosure. Further, separate references to "one embodiment" or "some embodiments" in this description do not necessarily refer to the same embodiment(s); however, neither are such embodiments mutually exclusive, unless so stated and except as will be readily apparent to those skilled in the art. Thus, this disclosure can include any variety of combinations and/or integrations of the embodiments disclosed herein. However, other embodiments of this disclosure may be directed to specific embodiments relating to each individual aspect, or specific combinations of these individual aspects. Thus, although this disclosure has been described with respect to specific embodiments, it will be appreciated that this disclosure is intended to cover all modifications and equivalents within the scope of the following claims.

Upon reading this detailed description, those of skill in the art will appreciate still additional alternative structural and functional designs for a system and method for compact data storage of network traffic and efficient search through the disclosed principles of the present disclosure. Thus, while particular embodiments and applications of the present disclosure have been illustrated and described, it is to be understood that this disclosure is not limited to the precise construction and components disclosed herein and that various modifications, changes and variations which will be apparent to those skilled in the art may be made in the arrangement, operation and details of the method and apparatus of the present disclosure herein without departing from the spirit and scope of this disclosure as defined in the appended claims.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

What is claimed is:

1. A method for masking private information captured during user interactions with a network site during a network session, the method comprising performing by a server:
   obtaining, from a capture agent operating on a user device, a set of captured user interactions with the network site during the network session, wherein the set of captured user interactions include (1) movements between portions of the network site and (2) data provided in one or more fields on the network site;
   identifying, by a scanning module of the server, instances of private information being included in the set of captured user interactions with the network site;
   assigning, for each of the instances of private information, a timestamp indicating a time of each instance of private information provided during the set of captured user interactions with the network site;
   loading, into a browser module, changes of a document object model (DOM) for the network site, the changes corresponding to the set of captured user interactions;
   identifying, for each of the instances of private information, a corresponding node in the document object model (DOM) for the network site using the timestamp assigned to each of the instances of private information; and
   providing information about each corresponding node to an additional module as part of a process for updating the capture agent to mask the corresponding node in future user interactions sent to the server.

2. The method of claim 1, further comprising:
   identifying, for each of the instances of private information, an information type included in each instance of private information; and
   identifying, for each of the instances of private information, a masking operation that corresponds with the information type of each instance of private information, wherein the information about each corresponding node includes masking operations for each of the instances of private information.

3. The method of claim 2, wherein the masking operation includes an encryption operation to encrypt private information such that the encrypted private information can be subsequently decrypted to securely access the private information.

4. The method of claim 2, wherein the masking operation includes a removal operation to remove private information.

5. The method of claim 1, wherein the instances of private information include text-based data provided in a field displayed on the network site.

6. The method of claim 1, further comprising:
   determining, for each corresponding node, that each corresponding node corresponds with a threshold number of previous network sessions identifying each corresponding node in the DOM for the network site; and
   adding each corresponding node that corresponds with the threshold number of previous network sessions to a blacklist to mask data in each corresponding node in subsequent network sessions.

7. The method of claim 1, wherein providing the information about each corresponding node to the additional module includes:
   sending the information to a user verification module capable of presenting the information about each corresponding node for confirmation of each corresponding node as including private information; and
   updating the capture agent to mask corresponding nodes that are confirmed as including private information by the user verification module.

8. The method of claim 1, further comprising:
   identifying a first field as relating to private information;
   determining whether a first value of the first field is common across a threshold number of network sessions; and
   ignoring the first field for masking in future sessions.

9. The method of claim 1, further comprising:
   filtering the set of captured user interactions using a filtering module, wherein the filtering module determines which of the set of captured user interactions satisfy at least one criterion, thereby determining filtered user interactions; and
   sending the filtered user interactions to the scanning module.

10. The method of claim 9, wherein the least one criterion includes one or more criteria of a page, the one or more criteria comprising a number of page views across users in a timeframe, an engagement metric providing a measure of user interaction with the page, a customer-specified criterion specifying a property of the page of the network site, or combinations thereof.

11. A system comprising:
   one or more processors; and
   a non-transitory computer-readable medium including instructions that, when executed by the one or more processors, cause the one or more processors to perform a method for masking private information captured during user interactions with a network site during a network session, the method including:
   obtaining, from a capture agent operating on a user device, a set of captured user interactions with the network site during the network session, wherein the set of captured user interactions include (1) movements between portions of the network site and (2) data provided in one or more fields on the network site;
   identifying, by a scanning module, instances of private information being included in the set of captured user interactions with the network site;
   assigning, for each of the instances of private information, a timestamp indicating a time of each instance of private information provided during the set of captured user interactions with the network site;
   loading, into a browser module, changes of a document object model (DOM) for the network site, the changes corresponding to the set of captured user interactions;
   identifying, for each of the instances of private information, a corresponding node in the document object model (DOM) for the network site using the timestamp assigned to each of the instances of private information; and
   providing information about each corresponding node to an additional module as part of a process for updating the capture agent to mask the corresponding node in future user interactions sent to the system.

12. The system of claim 11, wherein the method further includes:
   identifying, for each of the instances of private information, an information type included in each instance of private information; and
   identifying, for each of the instances of private information, a masking operation that corresponds with the information type of each instance of private information, wherein the information about each corresponding node includes masking operations for each of the instances of private information.

13. The system of claim 12, wherein the masking operation includes an encryption operation to encrypt private information such that the encrypted private information can be subsequently decrypted to securely access the private information.

14. The system of claim 12, wherein the masking operation includes a removal operation to remove private information.

15. The system of claim 11, wherein the instances of private information include text-based data provided in a field displayed on the network site.

16. The system of claim 11, wherein the method further includes:
   determining, for each corresponding node, that each corresponding node corresponds with a threshold number of previous network sessions identifying each corresponding node in the DOM for the network site; and
   adding each corresponding node that corresponds with the threshold number of previous network sessions to a blacklist to mask data in each corresponding node in subsequent network sessions.

17. The system of claim 11, wherein providing the information about each corresponding node to the additional module includes:
   sending the information to a user verification module capable of presenting the information about each corresponding node for confirmation of each corresponding node as including private information; and
   updating the capture agent to mask corresponding nodes that are confirmed as including private information by the user verification module.

18. The system of claim 11, wherein the method further includes:
   identifying a first field as relating to private information;
   determining whether a first value of the first field is common across a threshold number of network sessions; and
   ignoring the first field for masking in future sessions.

19. The system of claim 11, wherein the method further includes:
   filtering the set of captured user interactions using a filtering module, wherein the filtering module determines which of the set of captured user interactions satisfy at least one criterion, thereby determining filtered user interactions; and
   sending the filtered user interactions to the scanning module.

20. The system of claim 19, wherein the least one criterion includes one or more criteria of a page, the one or more criteria comprising a number of page views across users in a timeframe, an engagement metric providing a measure of user interaction with the page, a customer-specified criterion specifying a property of the page of the network site, or combinations thereof.

* * * * *